US009289528B2

(12) United States Patent
Nair et al.

(10) Patent No.: US 9,289,528 B2
(45) Date of Patent: Mar. 22, 2016

(54) METHODS FOR USING INDICATOR COMPOSITIONS

(71) Applicants: Mridula Nair, Penfield, NY (US); Kevin D. Lofftus, Fairport, NY (US); Mary Christine Brick, Webster, NY (US)

(72) Inventors: Mridula Nair, Penfield, NY (US); Kevin D. Lofftus, Fairport, NY (US); Mary Christine Brick, Webster, NY (US)

(73) Assignee: EASTMAN KODAK COMPANY, Rochester, NY (US)

( * ) Notice: Subject to any disclaimer, the term of this patent is extended or adjusted under 35 U.S.C. 154(b) by 205 days.

(21) Appl. No.: 13/927,164

(22) Filed: Jun. 26, 2013

(65) Prior Publication Data
US 2015/0004707 A1   Jan. 1, 2015

(51) Int. Cl.
*G01N 21/78* (2006.01)
*A61L 2/28* (2006.01)

(52) U.S. Cl.
CPC ........................................ *A61L 2/28* (2013.01)

(58) Field of Classification Search
CPC .......................................................... A61L 2/28
USPC ...................................... 436/1; 422/425, 429
See application file for complete search history.

(56) References Cited

U.S. PATENT DOCUMENTS

| 3,093,242 | A | | 6/1963 | Huyck et al. |
| 3,179,600 | A | * | 4/1965 | Brockett ........................ 503/200 |
| 3,469,439 | A | * | 9/1969 | Roberts et al. .................. 73/762 |
| 3,471,422 | A | | 10/1969 | Edlein et al. |
| 3,503,783 | A | * | 3/1970 | Evans ............................ 427/10 |
| 3,896,965 | A | * | 7/1975 | Cornell ....................... 220/359.2 |
| 4,091,921 | A | | 5/1978 | Lewis |
| 4,104,910 | A | * | 8/1978 | Ogata et al. ................. 73/862.53 |
| 4,121,714 | A | * | 10/1978 | Daly et al. ..................... 206/363 |
| 4,132,112 | A | * | 1/1979 | Hosoi et al. .................... 503/200 |
| 4,194,622 | A | * | 3/1980 | Lewis ............................ 206/363 |
| 4,356,149 | A | * | 10/1982 | Kitajima .................. C12Q 1/58 422/423 |
| 4,438,067 | A | * | 3/1984 | Siddiqi ................. G01N 33/521 422/429 |
| 4,495,291 | A | | 1/1985 | Lawton |
| 4,675,161 | A | * | 6/1987 | Hashimoto et al. ............ 422/401 |
| 4,780,411 | A | * | 10/1988 | Piejko .................. B01D 69/141 422/424 |
| 5,057,433 | A | | 10/1991 | Douglas |
| 5,059,261 | A | * | 10/1991 | Condo et al. ................ 149/19.92 |
| 5,325,721 | A | * | 7/1994 | Pendergrass, Jr. .............. 73/762 |
| 5,340,537 | A | | 8/1994 | Barrett |
| 5,344,017 | A | | 9/1994 | Wittrock |
| 5,756,356 | A | * | 5/1998 | Yanagi et al. ....................... 436/7 |
| 5,804,298 | A | * | 9/1998 | Moy ......................... B01J 13/02 428/321.5 |
| 6,395,551 | B1 | * | 5/2002 | Kipke et al. ....................... 436/1 |
| 6,488,890 | B1 | | 12/2002 | Kirckof |
| 7,294,379 | B2 | | 11/2007 | Ko et al. |
| 7,790,225 | B1 | * | 9/2010 | Calle et al. ..................... 427/212 |
| 8,110,628 | B1 | | 2/2012 | Nair et al. |
| 8,183,045 | B2 | | 5/2012 | Faran |
| 8,569,208 | B1 | * | 10/2013 | Ribi ............................. 503/216 |
| 2003/0068824 | A1 | * | 4/2003 | Frankel et al. .................. 436/60 |
| 2004/0241862 | A1 | * | 12/2004 | Puntambekar .................... 436/1 |
| 2007/0166542 | A1 | * | 7/2007 | Braun et al. ............. 428/402.21 |
| 2007/0197383 | A1 | * | 8/2007 | Koene et al. ................. 503/201 |
| 2009/0123332 | A1 | | 5/2009 | Whitehead et al. |
| 2009/0181254 | A1 | * | 7/2009 | White et al. ................ 428/402.2 |
| 2009/0181466 | A1 | * | 7/2009 | Wenzel et al. ................ 436/163 |
| 2009/0220378 | A1 | | 9/2009 | McDonnell et al. |
| 2009/0301382 | A1 | * | 12/2009 | Patel ............................. 116/201 |
| 2009/0304905 | A1 | * | 12/2009 | Graham et al. .................... 427/8 |
| 2010/0151577 | A1 | * | 6/2010 | Davis et al. ....................... 436/6 |
| 2010/0326198 | A1 | * | 12/2010 | Ribi ............................... 73/700 |
| 2010/0331445 | A1 | * | 12/2010 | Wilson et al. ................. 523/116 |
| 2011/0312096 | A1 | * | 12/2011 | Whitman et al. .................. 436/1 |
| 2012/0196373 | A1 | * | 8/2012 | Odom et al. ...................... 436/2 |
| 2012/0205269 | A1 | | 8/2012 | Ludvig |
| 2013/0017612 | A1 | * | 1/2013 | Li et al. ........................... 436/75 |

FOREIGN PATENT DOCUMENTS

GB    1 458 553    12/1976
JP    2008-094401    4/2008

* cited by examiner

*Primary Examiner* — Arlen Soderquist
(74) *Attorney, Agent, or Firm* — J. Lanny Tucker

(57) ABSTRACT

An indicator composition can be exposed to various environmental conditions stimuli such as in sterilization or storage processes. This indicator composition has a) a first polymeric particle comprising a solid continuous polymeric phase and a first reactant, the first polymeric particle having a mode particle size equal to or less than 50 μm; and b) a second reactant outside of the first polymeric particle, which second reactant is capable of reacting with the first reactant when exposed to a chosen environmental condition stimulus. The indicator composition can be used by exposing it to the environmental condition stimulus for a sufficient time to cause a detectable change in the indicator composition such as a detectable color change.

16 Claims, No Drawings

METHODS FOR USING INDICATOR COMPOSITIONS

RELATED APPLICATION

Copending and commonly assigned U.S. Ser. No. 13/927,139 filed on Jun. 26, 2013, by Nair, Lofftus, and Brick, and entitled REACTIVE INDICATOR COMPOSITIONS AND ARTICLES CONTAINING SAME.

FIELD OF THE INVENTION

This invention relates to methods for using indicator compositions that include two different reactants, at least one reactant being within a polymeric particle and a second reactant being isolated from the first reactant.

BACKGROUND OF THE INVENTION

Indicator compositions and devices are used in many industries such as the medical, dental, veterinary, and food industries, to provide evidence regarding the history of a product's exposure to various environmental conditions. Although electronic devices are available to monitor environmental conditions, such as temperature, humidity, pressure, UV exposure, pollutants, and others like these, such devices are typically too expensive to incorporate into individual packages. Thus, simpler indicator compositions and devices using inexpensive chemistry provide a more economical way to monitor exposure to environmental conditions.

In some uses, an indicator composition is designed to provide a warning that a product has been exposed to unwanted environmental conditions. For example, meat and dairy products can include a sensor derived from an indicator composition designed to reveal unsafe exposures to certain temperatures over a period of time. These indicator compositions are sometimes known as "time-temperature indicators" or TTI's. Such TTI's can be used for monitoring time and temperature exposures of a wide variety of items including food and medical products. Unlike expiration dates on products, which are merely recommendation dates based on expected transport and storage conditions that are unknown to the consumer, TTI's can be designed to respond directly to the temperature to which the product is exposed and then reflect the actual temperature history of the product. Commercial distributors of food and pharmaceuticals commonly attach or print TTI's onto shipping boxes. The most common purpose is to ensure the integrity of the supply chain from manufacturer to the customer.

A TTI can be matched to a particular perishable product or to a particular use. Examples of perishable products for which the use of such device can be useful include but are not limited to, packaged fresh and frozen foods, dairy products, meat, pharmaceuticals, photographic film, canned goods, spices, vitamins, seeds, and plants. Other products that slowly degrade over time, and for which TTI's are useful, include paints, coatings, adhesives, caulks, and other sealants.

Temperature indicators are basically grouped into two families. A first group can signal a change only after a certain critical temperature has been reached or exceeded (threshold). A second group (such as in a TTI) can be designed to integrate over the entire temperature range and then signal a condition at any stage.

In one instance, the indicator composition is designed to provide affirmation that a desired environmental conditioning has been achieved, for example as sterilization or as cocking indicators. In hospitals, clinics, and other medical facilities, it is standard practice to sterilize various articles such as gowns, drapes, sheets, dressings, and other articles, prior to use by placing them in an autoclave where they are subjected to steam sterilization. It is common practice in sterilizing such articles to gather several articles together, bundling them in a porous wrap as a package, and placing them in an autoclave together with a sterilizing indicator article or device. This indicator device can be either inserted into or applied to the package of articles. Where pressure-sensitive adhesive tapes are used to bundle the articles, it is convenient to arrange the indicator composition on the back of the adhesive tape.

The Association fir the Advancement of Medical Instrumentation {AAMI} has recommended practices and standards that cover sterilization testing, including the use of chemical indicator compositions. AAMI categorizes chemical indicator compositions in six classes as described in Sterilization of Health Care Products—Chemical Indicators—Part 1: General Requirements, American National Standards Institute (ANSI)/AAMI ST 60-(1996). Class 1 relates to process indicators that are intended for use with individual packs to demonstrate that the pack has been exposed to the sterilization process and to distinguish between processed and unprocessed packs. Class 2 describes indicators for use in a specific test procedure such as a Bowie-Dick test. Class 3 relates to single parameter indicators to indicate exposure to a sterilization process at a stated value (SV) of the chosen parameter, and Class 4 relates to multi-parameter indicators that are designed to respond to two or more critical parameters and is intended to indicate exposure to a sterilization cycle at SV's of the chosen parameters (for example, time, temperature and saturated steam as critical conditions for a steam cycle). Class 5 chemical indicators are known as integrating indicators that are designed to react in response to all critical parameters over a specific range of sterilization cycles and whose performance has been correlated to the performance of the relevant biological indicator under the labeled conditions of use. Class 6 chemical indicators are emulating indicators that are intended for cycle verification and are designed to react to all critical parameters for specified sterilization cycles. They are considered to be indicative of a complete cycle by showing the presence or absence of specific time and temperature parameters during a cycle.

Surgical instruments used in medical, dental and veterinary applications are reused after sterilization in appropriate pouches. The surgical instruments can be sterilized inside a pouch using a variety of sterilizing agents such as ethylene oxide and steam. A sterilization indicator composition can be provided inside or on the pouch, for example using a printing operation, to provide a sterilization history. For example, it is common practice to sterilize surgical instruments by sealing them in vapor-permeable plastic and exposing the packaged surgical instruments to hot steam for a certain period of time. To be sure that the surgical instruments have had the appropriate exposure to steam and temperature for the requisite time, color-changing indicator compositions in the form of patches can be provided inside of the package with the surgical instruments. Typically, steam-based sterilization indicators include two active components that react with each other (at high temperature steam) to provide a color change. In some cases, however, the color-changing indicators compositions indicate a color change prematurely, giving a false indication of sterilization. To control or adjust the reactivity of the color-changing indicator compositions, one can consider altering the chemical reactants to be more stable, but this can be difficult and bring more unpredictability to the situation.

A number of efforts have been made to solve the problem noted above where "false positives" are obtained with known sterilization indicator compositions. For example, it has been desired to find an inexpensive and effective way to keep reactants separated before their reaction is needed in response to a specific environmental conditions or stimulus.

U.S. Pat. No. 8,110,628 (Nair et al.) describes the incorporation of different reactants in different pores of polymeric particles, but there is no enabling teaching as to how such distinctly isolated reactants can be used in indicator compositions.

U.S. Pat. No. 7,585,521 (Barbe et al.) describes the preparation of controlled release ceramic particles, but it fails to describe how active materials within the ceramic particles can be used in indicator compositions.

U.S. Patent Application Publication 2009/0220378 (McDonnell et al.) discloses an indicator device for determining the efficacy of an antimicrobial treatment process. The indicator device includes an active agent incorporated within an electrospun polymeric nanofiber. Copper sulfate is mentioned as a possible incorporated reactant. Nanofiber devices can be used in limited procedures.

U.S. Pat. No. 5,340,537 (Barrett) discloses temperature indicating compositions that include an aqueous binder, a color changing electron donating compound having a high melting point, and a polymeric electron accepting resin reactive with the electron donating compound.

U.S. Pat. No. 7,294,379 (Ko et al.) describes a time indicating label comprising (a) a label substrate having first and second surfaces, (b) an acid-base indicator composition, and (c) an activator composition, wherein one of (b) or (c) is on the first surface of the substrate. When (b) and (c) are brought into contact, they remain adhered and can be detected. The activator can be, for example, an organic sulfonic acid.

U.S. Pat. No. 8,183,045 (Faran) discloses a device allegedly capable of exhibiting a time-temperature dependence that comprises an upper layer carrying a first reactant selected from a group of materials such as chelating agents and a base layer carrying a second reactant adapted to react with the first reactant upon triggering. The device provides two reactants in different layers with a polymeric barrier layer between them and one of the reactants can diffuse through the barrier to react with the other.

WO2011/020185 (AR Medicom Inc.) discloses a sterilization pouch for surgical instruments that comprises a sterilant permeable sheet with a first sealing strip and a sterilant impermeable sheet with a second sealing strip. The sealing strips are sealed together to define the pouch. An indicator composition for indicating sterile processing conditions inside the pouch is located on an inner surface of the sterilant impermeable sheet.

While chemical indicator chemicals are known, it is difficult for a single material to have the precise reactivity properties needed to accurately monitor environmental conditions when the packaging used for sterilization varies from product to product. For some uses, an indicator composition is needed outside the packaging while for other uses it is needed inside the packaging. The packaging can be designed with paper or polymers, which materials have differing chemical permeabilities and thermal conductivities. Thus, when there is a need to alter or adapt the reactivity of the indicator composition to different packaging arrangements, the indicator compositions are generally prepared using different sets of chemicals. A simple system is needed wherein the reactivity of an indicator composition can be easily adapted for various applications in various packages without using a large number of alternative chemical components.

In many sterilization processes, such as sterilization of surgical instruments, indicator compositions for steam sterilization are designed to provide a visual color change after contact with saturated steam at high temperature for a specified period of time sufficient bacterial kill for Class 4 and 5 indicators. A disadvantage with known steam sterilization indicator compositions is that indicator inks can change color prematurely.

There is a need for indicator compositions that are not triggered prematurely and that can be used to accurately determine when chosen environmental conditions or multi-parameters are met. It is also desired that indicator compositions and devices are provided with simple indicator chemistry for a variety of packaging arrangements and thus can be used in various indicating methods.

SUMMARY OF THE INVENTION

The present invention provides a method for indicating an environmental condition stimulus, the method comprising:

exposing an indicator composition to an environmental condition stimulus to cause a detectable change in the indicator composition, the indicator composition comprising:

a) a first polymeric particle comprising a solid continuous polymeric phase and a first reactant, the first polymeric particle having a mode particle size equal to or less than 50 µm; and b) a second reactant outside of the first polymeric particle, which second reactant is capable of reacting with the first reactant when exposed to an environmental condition stimulus.

The present invention provides a number of advantages and advances in the art. For example, the present invention provides a means for controlling the kinetics (reaction rates) of various reactants that are incorporated within indicator compositions, upon response to various environmental stimuli such as temperature, chemicals, humidity, bacteria, viruses, fungi, and radiation. Such environmental conditions can then be detected for various industrial purposes and particularly to indicate when medical equipment and clothing has been effectively sterilized for flit ire use.

In addition, the present invention improves the stability of an indicator composition with time, for example after the indicator composition is printed or otherwise applied onto a substrate such as a plastic film or pouch surface.

DETAILED DESCRIPTION OF THE INVENTION

Definitions

As used herein to define various components of the polymeric particles, reactants, formulations and layers, unless otherwise indicated, the singular forms "a", "an", and "the" are intended to include one or more of the components (that is, including plurality referents).

Each term that is not explicitly defined in the present application is to be understood to have a meaning that is commonly accepted by those skilled in the art. If the construction of a term would render it meaningless or essentially meaningless in its context, the definition of the term should be taken from a standard dictionary.

The use of numerical values in the various ranges specified herein, unless otherwise expressly indicated otherwise, are considered to be approximations as though the minimum and maximum values within the stated ranges were both preceded by the word "about". In this manner, slight variations above and below the stated ranges can be used to achieve substantially the same results as the values within the ranges. In addition, the disclosure of these ranges is intended as a continuous range including every value between the minimum and maximum values.

The term "sterilant" refers to a chemical, combination of chemicals, or procedure that provides sterilization in a given situation. In other words, a sterilant can be an environmental condition stimulus or be used in a procedure that is an environmental condition stimulus that causes a described reaction of the first and second reactants as described herein.

Sterilization can be conducted in a variety of ways and include procedures that utilize different sterilizing agents or procedures using one or more environmental conditions that stimulate a change such as a chemical or color change. For example, useful environmental condition stimuli include but are not limited to hydrogen peroxide, peracetic acid, glutaraldehyde, ozone, saturated steam, dry heat at a temperature greater than 100° C., ethylene oxide, formaldehyde, and electromagnetic radiation such as gamma irradiation as a sterilant or as an element or step in the procedure, as well as those sterilization procedures that utilize combinations of such sterilizing agents or procedures. The present invention can be practiced using these sterilants or with procedures that utilize pressurized saturated steam, for example steam at 135° C., as the sterilant. This procedure is known herein the steam sterilization procedure that can be used to sterilize medical, dental, or veterinary instruments or clothing.

As used herein, a steam sterilization indicator composition is a material or a combination of materials that responds to a steam sterilization procedure such that the indicator composition is capable of having a first indicating state prior to being exposed to a predetermined sterilization procedure and a second indicating state after exposure to at least a portion of the sterilization procedure (such as the entire sterilization procedure). For example, the first indicating state of the indicator composition can be a first color and the second indicating state of the indicator composition can be a second color that is different from the first color. The first indicating state can also be a substantially clear or transparent or translucent state, and the second indicating state can be a substantially opaque or colored state. The converse of these indicating states can also be used in the practice of this invention. In some other embodiments, the chemical reaction from sterilization can be the production of a color that hides or obscures an original color of one or both reactants or of an inert colorant.

In some embodiments, porous organic polymeric particles containing discrete compartments are used in the indicator compositions described herein. Such porous organic polymeric particles are generally prepared, as described below, using multiple water-in-oil emulsions in combination with an aqueous suspension process, such as in the ELC process. For example, the various details for preparation of these porous organic polymeric particles are provided in the U.S. Patent Application Publications 2008/0176157 (Nair et al.) and 2010/0021838 (Putnam et al) and U.S. Pat. No. 7,754,409 (Nair et al.) and U.S. Pat. No. 8,100,628 (noted above), the disclosures of all of which are incorporated herein by reference. Some details of such processes are described below.

In other embodiments, porous inorganic polymeric particles are used in the indicator compositions described herein. Such porous inorganic polymeric particles can be prepared using a multiple emulsion process such as a water-in-oil emulsion in combination with an aqueous suspension process, or multiple oil-in-water emulsions in combination with an oil suspension process (water-in-oil-in-water) or an oil-in-water emulsion in combination with an oil suspension process (oil-in-water-in-oil). In either process, the continuous phase of the first emulsion is typically derived from a sol-gel based process in which alkoxides of suitable elements (including transition metals, and silicon) are hydrolyzed and condensed to form a sol. This sol is further condensed to form a gel network. The porous inorganic polymeric particles can also be prepared using a single water-in-oil emulsion or a single oil-in-water emulsion. In either process, the dispersed phase is typically derived from a sol-gel based process in which alkoxides of suitable elements (including transition metals, and silicon) are hydrolyzed and condensed to form a sol. This sol is further condensed to form a gel network. Further details for making such porous inorganic polymeric particles from multiple emulsions are provided in U.S. Pat. No. 8,394,396 (Brick et al.), the disclosure of which is incorporated herein by reference. Further details for making such porous inorganic polymeric particles from a single emulsion are provided in "Preparation of SiO2-TiO2 Spherical Particles by W/O-Type Emulsion Technique" by Moriya et al., *Journal of The Ceramic Society of Japan*, Int. Edition, 1995, vol. 103, pp. 570-575.

In still other embodiments, the indicator compositions can comprise non-porous organic polymeric particles that can be prepared for example the evaporative limited coalescence (ELC) process described in U.S. Pat. No. 4,833,060 (Nair et al.), and U.S. Pat. No. 4,965,131 (Nair et al.), the disclosures of which are hereby incorporated by reference.

Unless otherwise indicated, the terms "compartment" and "pore" are intended to mean the same thing, a void in a porous organic or inorganic porous polymeric particle that has a definable volume. Each polymeric particle of this type will contain at least one compartment, but more likely, each polymeric particle will comprise multiple discrete compartments that are not interconnected and that have inner walls formed by the solid continuous polymeric phase.

The terms "porous particle" and "porous particles" are used herein, unless otherwise indicated, to refer to organic or inorganic polymeric materials useful in the indicator compositions described herein. The porous particles generally comprise a solid continuous organic or inorganic polymeric phase having an external particle surface and discrete compartments dispersed within the continuous solid phase and a first reactant can be disposed exclusively within the volume of one or more discrete compartments.

The term "non-porous" refers to organic or inorganic polymeric particles that are not designed to have discrete compartments within the solid continuous polymeric phase and less than 5% of their total volume consists of compartments, pores, or voids. In one embodiment, the solid continuous polymeric phase of the inorganic polymeric particles can contain a uniform distribution of meso pores.

The solid continuous polymeric phase of the porous organic or in organic polymeric particles generally has the same composition throughout the phase. That is, the solid continuous polymeric phase is generally uniform in composition including any additives (for example, insert colorants) and first reactants that can be incorporated therein. In addition, if mixtures of polymers are used in the solid continuous polymeric phase, generally those mixtures are dispersed uniformly throughout.

The term "porogen" refers to a pore forming agent used to make porous organic and inorganic polymeric particles. A porogen can be the aqueous phase of the water-in-oil emulsions (that is the first aqueous phase), the pore stabilizing hydrocolloid, and any other additive in the aqueous phase that can modulate the porosity of the porous inorganic or organic particles. When using an oil-in-water-in-oil process, a porogen can be the oil phase of the oil-in-water emulsion (that is the first oil phase), including any pore stabilizing materials, and any other additive in the oil phase that can modulate the porosity of the porous inorganic or organic particles.

The term "discrete compartments" refers to isolated compartments in a porous inorganic or organic particle.

The term "size" refers to the modal or average diameter when referring to particles or compartments.

The porous organic and inorganic polymeric particles can include "micro", "meso", and "macro" compartments, which according to the International Union of Pure and Applied Chemistry, are the classifications recommended for compartment sizes of less than 2 nm, from 2 to 50 nm, and greater than 50 nm, respectively. Thus, while the porous organic or inorganic polymeric particles can include closed compartments of all sizes and shapes (compartments entirely within the solid continuous polymer phase) providing a suitable volume in each compartment, macro pores are the preferred close compartments. While there may be open macro porous compartments on the surface of the porous organic or norganic polymeric particle, such open compartments are not desirable and can be present only by accident. The size of the particle, the formulation, and manufacturing conditions are the primary controlling factors for compartment size. However, typically the discrete compartments independently have an average compartment size of at least 100 nm and up to and including 4 µm, or more likely at least 200 nm and up to and including 2 µm. For spherical compartments, this average compartment size is an "average diameter". For non-spherical compartments, the average compartment size refers to the "average largest dimension". Average compartment size can be determined by analyzing Scanning Electron Microscopy (SEM) images of fractured porous inorganic or organic polymeric particles using a commercial statistical analysis software package to study the distribution of the compartments within the particles, or by manually measuring the compartment diameters using the scale in the SEM images. For example, the average compartment size can be determined by calculating the average diameter of at least 20 measured compartments in a single porous organic or inorganic polymeric particle.

The porous organic and inorganic polymeric particles used in this invention generally have porosity of at least 5% and up to and including 80%, or more likely at least 10% and up to and including 50%, or typically at least 10% and up to an including 30%, all based on the total particle volume. Porosity can be measured by the mercury intrusion technique.

Indicator Compositions

The indicator con positions can be used in various applications as described herein. For example, the indicator compositions can be used in the form of indicia that is printed, ink jetted, or otherwise applied onto one of the layers of an article, such as a tape, web, label, card, paper stripe, pouch, package, or other device that could be used in a sterilization article, device, or process as readily apparent to one skilled in the art. For example, the indicator composition can be applied as a label to a part of the article. Alternatively, the indicator composition can be located on a paper or polymeric film substrate (or support) on the inside of a transparent polymeric sheet or film of a pouch (such as a sterilization pouch), or between polymeric films or layers (formed as laminate) within a pouch.

Some embodiments of useful sterilization pouches in which the present invention can be used include those described in U.S. Pat. No. 5,344,017 (Whittrock) and in U.S. Patent Application Publications 2009/0123332 (Whitehead et al.) and 2012/0206269 (Ludvig), all of which disclosures are incorporated herein by reference.

In some embodiments, the indicator composition is applied to a suitable substrate or material, such as a polymeric film, paper, or other material, and the indicator composition is further overcoated with a protective polymeric layer in order to prevent contact of the indicator composition and its components (either or both first and second reactants) with the article to be sterilized. When applied to the inner surface of the substrate inside the article (for example, pouch) such an embodiment also allows the indicator composition or components to be used internally within the same compartment of the article (for example, pouch) to be sterilized or subjected to environmental conditions.

The applied or incorporated indicator composition can undergo a visibly perceptible color change when exposed to an environmental condition stimulus, for example to provide a desired end color to indicate that successful sterilization has occurred using the indicator composition. For example, a steam sterilization process can produce a color change from one designated original color such as pink to another chosen color (depending upon chemical reactants), such as a readily distinguishable dark brown, upon sufficient exposure to complete sterilization conditions (that is, when exposed to a complete multi-parameter steam sterilization process). The desired transition to the desired end color (a "designated end color change") can be caused by a chemical reaction between first and second reactants, such as a copper or lead compound reacting with a source of sulfide ion to produce copper or lead sulfide, respectively.

Thus, as contemplated for this invention, a detectable "color change" can represent a change from a colorless state to a colored state, a change from a colored state to a colorless state, a change from one color hue to another color hue, or a combination of any of these changes. These color changes can also include a chemical change that "hides" an original color in the indicator composition.

Polymeric Particles:

In general, the indicator composition used in this invention comprises a) a first polymeric particle (described below) comprising a first reactant, and b) a second reactant that is outside the first polymeric particle. This second reactant is capable of reacting with the first reactant when it is exposed to an environmental condition stimulus (as described above). The first reactant can be incorporated within the solid continuous polymer phase of the first polymeric particle. Alternatively, the first reactant can be incorporated into one or more discrete compartments within the first polymeric particle. Still again, the first reactant can be incorporated in both the solid continuous polymeric phase and in one or more discrete compartments.

A first reactant is incorporated into the first polymeric particle in an amount of at least 0.1 weight % and up to and including 50 weight %, or at least 1 weight % and up to and including 40 weight %. The amount of the first reactant can be optimized for a given first reactant-second reactant combination and the particular sterilization process in which it is to be used. The teaching in this disclosure provides sufficient guidance for a skilled worker to appropriately choose the reactants and amounts, and where they are incorporated (within or without polymeric particles).

The first polymeric particle used in the present invention has a mode particle size equal to or less than 50 µm, or at least 1 µm and up to and including 50 µm, or even at least 1 µm and up to and including 20 µm.

In many embodiments, the first polymeric particle comprising the first reactant can have one or more discrete compartments and the first reactant is provided within the volume of at least one of these discrete compartments. The one or more discrete compartments can have an average compartment size of less than 4 μm or at least 200 nm and up to and including 2 μm.

The first polymeric particles (porous and nonporous embodiments) are described in more detail below in the discussion relating to the formation of polymeric particles (both organic and inorganic polymeric particles). In many embodiments, the solid continuous organic polymeric phase of the first polymeric particle is composed of one or more organic polymers (described in detail below), such as polyesters, cellulose polymers, acrylic polymers (formed from one or more ethylenically unsaturated polymerizable monomers), styrene-acrylic copolymers, or a mixture thereof. Further details of such porous organic polymeric particles are provided below.

In other embodiments, the first polymeric particle is composed of one or more inorganic polymers (as described below). For example, the inorganic polymer can be a silica-containing polymer. Details of some of such porous inorganic polymeric particles are provided in U.S. Pat. No. 8,394,396 (noted above).

In still other embodiments, the first polymeric particle can comprise a mixture of at least one organic polymer and at least one inorganic polymer.

Organic Polymeric Matrix:

The indicator composition can also comprise an organic polymeric matrix in which one or more first polymeric particles and the second reactant are dispersed. This organic polymeric matrix can be water-soluble or water-dispersible and can include one or more organic polymers that are generally neutral in charge. Thus, such organic polymers are preferably nonionic and in some embodiments do not contain acidic groups such as carboxylic acid and basic groups such as amine groups. Useful organic polymers include but are not limited, to poly(vinyl alcohol), poly(vinyl pyrrolidone), ethylene oxide polymers, polyurethanes, urethane-acrylic copolymers, other acrylic polymers, styrene-acrylic copolymers, vinyl polymers, and polyesters, or a combination of two or more of these organic polymers. Such organic polymeric materials are readily available from various commercial sources or prepared using known starting materials and synthetic conditions. The organic polymeric matrix is useful in the indicator composition for adhering the first polymeric particles and second reactant onto a substrate. The organic polymeric matrix can also be used to provide integrity to an applied film of indicator composition. The organic polymeric matrix can be used to prevent the indicator composition from being easily removed or washed away under the conditions of sterilization, such as during the use of saturated steam or high dry heat. In addition, the organic polymeric matrix provides spacing between the first reactant in the first polymeric particles and the second reactant, thus providing another means for controlling the timing of reaction (for example, by controlling the timing or duration of color change) during the sterilization processes.

When present, the organic polymeric matrix can be present in an amount of at least 1 weight % and up to and including 75 weight %, or typically at least 5 weight % and up to and including 50 weight %, of the total dry indicator composition weight.

First and Second Reactants:

The first and second reactants can be chosen from any suitable combination of chemicals that will react under a suitable environmental condition stimulus and such interaction causes a detectable change to occur, such as detectable color change as described above. The present invention is not limited to only the specific environmental condition stimuli and the detectable changes described herein but these are described as representative and as guidance for a skilled worker to devise other obvious combinations of first and second reactants for a specific environmental condition.

One useful embodiment involves first milling both the first and second reactants of the indicator composition to a fine particle size, then encapsulating one reactant (for example, first reactant) in the compartments of a porous organic or inorganic polymeric particle and then incorporating the other reactant (for example, a second reactant) within an organic polymeric matrix in a simple one-step coating process.

While the first reactant is always inside the first polymeric particle, the second reactant is always outside that first polymeric particle. It is possible for the second reactant to be incorporated and used within a different (second) polymeric particle. Examples of these embodiments are described below. The second polymeric particle can have the same or different chemical composition as the first polymeric particle. Either or both first and second polymeric particles can be either non-porous or porous as defined herein. For example, the second polymeric particles can comprise one or more discrete compartments of the same or different average compartment size as the discrete compartments in the first polymeric particles. The second reactant can be in one or more of the discrete compartments in the second polymeric particles as long as it or its reaction intermediates can escape for reaction with the first reactant. In other embodiments, the second reagent can be present in the solid continuous polymeric phase of the second polymeric particle, or in both the solid continuous polymeric phase and in one or more discrete compartments.

Alternatively, the second reagent can be supplied and used in the indicator composition outside of a polymeric particle, for example as a non-incorporated second reagent dispersed within the organic polymeric matrix.

The first and second reactants can be provided in any suitable form, liquid, gaseous, or solid, as one skilled in the art would appreciate from the teaching provided herein. In many embodiments, the first reactant is provided as a solid chemical (particulate) or in a liquid dispersion of solution within the discrete compartments of the first polymeric particle. The second reactant can be similarly provided in a second polymeric particle of the same or different size and composition as the first polymeric particle described herein.

The first reactant can also be a precursor to or derivative or reaction intermediate of a chemical compound that will react with the second reactant. For example, such "first reactant precursors" can include but are not limited to, barium thiosulfate, elemental sulfur, and zinc sulfide.

As one embodiment for steam sterilization, at least one sulfur-containing compound that is a source for sulfide ions can be used as a first reactant. Such first reactants include but are not limited to, thiosulfates including but are not limited to barium thiosulfate, polythionates, sulfur, episulfides, thioesters, disulfides, and inorganic sulfides including but not limited to zinc sulfide. Useful second reactants include but are not limited to metal salts, for example basic copper carbonate, lead salts, and silver salts that are reactive with sulfide ion including those that are particularly reactive in the presence of elemental sulfur to form visually dark metal sulfides. For example, zinc sulfide can be reacted in the presence of elemental sulfur to produce copper sulfide under steam sterilization conditions, thus resulting in a pronounced color change. Examples include salts and complexes containing copper, lead, iron, nickel, bismuth, silver, or chromium or any combinations of two or more of these metals. Copper and lead are particularly useful as metal salts or metal-containing complexes. The metal salts can be provided in any convenient form such the carbonate, nitrate, chloride, bromide, sulfate or other salt that would be readily apparent to one skilled in the art. Metal carbonates are particularly useful.

Some examples of such color change causing first and second reactant combinations and reactions are disclosed in U.S. Pat. No. 5,057,433 (Douglas) and U.S. Pat. No. 6,488,890 (Kirckof), the disclosures of which are incorporated herein by reference. Metal sulfides tend to be strongly colored and are often the most stable form of metal sulfur-containing compounds. Furthermore, they are often insoluble in water and can be incorporated into a binder to prevent staining of components in a device or article of the present invention. As mentioned before, in one embodiment, elemental sulfur is included with another sulfur source such as a sulfide as the first reactant.

Although such sulfur-containing compounds and sulfide-reactive metal salts are used together as a (homogeneous) mixture or as a single composition in known sterilization processes, in the present invention the first and second reactants are kept separated until the sterilization conditions cause them to interact. For example, in one particularly useful embodiment, a sulfur source is provided in a first polymeric particle and the second reactant (a metal source reactive with a sulfide anion) is provided outside the first polymeric particle according to the present invention. The metal source can be conveniently provided as a metal salt or complex and any sulfide-forming metal-containing material can be used.

Sets of useful indicator compositions include those having first and second reactants that form a metal complex with a corresponding change in properties, for example a color change (absorbance, luminescence, or fluorescence). Examples of such compositions are found in U.S. Pat. No. 5,064,576 (Suto), the disclosure of which is incorporated herein by reference. Under appropriate time and temperature or steam, time, and temperature conditions, a first metal complex can undergo a ligand exchange to form a second metal complex. In one embodiment, the steam sensitive indicator composition contains a metal complex and an exchange ligand as first and second reactants. For example, a useful metal complex is bis(dimethylglyoximato)nickel, bis(2-furyldioximato) nickel, zirconium chloroanilate, or bis(nioximato) nickel. The exchange ligand in this embodiment can be either 1) an aminocarboxylic acid which comprises from 1 to 6 carboxylic acid groups and from 1 to 4 amino groups, and its salts, or 2) citric or tartaric acids and their salts.

In a related embodiment, an uncomplexed metal salt can react with a ligand to form a metal complex that is detectably different from the uncomplexed metal salt, for example, having a different color (absorbance or fluorescence). For example, ferrous salts can react with bipyridyl ligands to form a red colored complex. Many other examples of color changing causing first and second reactants are known in the art, and one of each set of reactants can be incorporated into the first polymeric particle.

Other indicator compositions can be designed to respond to pH changes. For example, first and second reactants can include an acid or base used with a pH indicator dye. U.S. Pat. No. 7,294,379 (noted above), the disclosure of which is incorporated herein by reference, describes some examples of such indicator composition first and second reactants that are useful in the practice of the present invention.

Still other indicator compositions can include first and second reactant pairs including an oxidant and a reductant. These reactants chemically react to change various properties such as a cause of or change in absorbance or emission. U.S. Pat. No. 5,340,537 (noted above), the disclosure of which is incorporated herein by reference, provides some useful examples of such reactants that can be adapted for use in the present invention.

U.S. Pat. No. 4,240,926 (McNeely) discloses a composition capable of recording steam and dry heat sterilizations and capable of differentiating there between, comprising combinations of first and second reactant pairs such as:

a reactant combination of thiobarbituric acid and parabanic acid, to form a colored product, and a reactant combination of thiobarbituric acid and a mixture of dimethyl oxalate and urea, to form a colored product.

Besides the essential first polymeric particle and the first and second reactants, and the optional and important organic polymeric matrix, the indicator composition used in this invention can also include various addenda that are optional but that can provide a useful purpose in certain embodiments.

For example, the indicator composition can comprise one or more inert colorants, meaning colored materials that do not participate in the reaction of first and second reactants in response to the environmental condition stimulus, but provides suitable visualization. Such inert colorants can include but are not limited to pigments and dyes of a desired hue, and these can be used to provide a visible mark showing the placement of an otherwise colorless indicator composition on an article or device to be subjected to sterilization conditions. In some embodiments, the color obtained from reaction of the first and second reactants during sterilization can mask or hide the incorporated (original) colorant and this can also be one way for the observer to know that sterilization has occurred.

Thus, one function of an inert colorant in an otherwise colorless indicator composition is to enable the user to locate the position of the indicator composition before sterilization. Another function is to enhance the color change by generating a color hue change that is more readily defined than a change from only the reaction of the first and second reactants during the sterilization.

The one or more inert colorants can be present within the first polymeric particle, a second polymeric particle, or within the organic polymeric matrix, of the one or more inert colorants can be present in multiple places within the indicator composition.

When one or more inert colorants are present in any of these locations of the indicator composition, they are present in an amount of at least 0.01 weight % and up to and including 10 weight %, or typically at least 0.1 weight % and up to and including 3 weight %, based on the total dry weight of the indicator composition. Examples of useful inert colorants include but are not limited to, organic and inorganic pigments such as, Pigment Violet 3, Pigment Violet 19, Pigment Violet 23, Pigment Red 122, Pigment Red 185, Pigment Red 177, Pigment Red 254, Pigment Blue 15, Pigment Blue 60, Pigment Green 7, Pigment Green 36, Pigment Orange 38, Pigment Orange 64, Chromopthal Magenta 2BC, Pigment Violet 47, Pigment Blue 27, Pigment Red 101, Pigment Red 102, and Pigment Green 15.

Other optional components of the indicator composition include but are not limited to, surfactants, humectants, coalescing agents, thickeners, and by-products from the preparation of the various polymers in the polymeric particles or organic polymeric matrix.

Polymeric Particles with Discrete Compartments

Methods for generating discrete compartments inside organic and inorganic polymeric particles have been disclosed in numerous publications, for example in U.S. Patent Application Publications 2008/0176157 and 2010/0021838 and U.S. Pat. Nos. 7,754,409, 8,100,628, and 8,394,396 (all noted above).

For example, porous organic polymeric particles with effective reactant location control and controlled particle size and particle size distribution are possible using a multiple emulsion process, in conjunction with a suspension process, particularly, the evaporative limited coalescence (ELC) process. While the present invention is described primarily with respect to use of these porous organic polymeric particles in indicator compositions useful in saturated steam sterilization applications, the invention is not limited to such embodiments.

The first polymeric particle used in the indicator composition has a mode particle size equal to or less than 50 µm, or of at least 1 µm and up to and including 50 µm or typically of at least 1 µm and up to and including 20 µm. Most useful polymeric particles, especially porous organic polymeric particles, have a mode particle size of at least 1 µm and up to and including 10 µm. Mode particle size represents the most frequently occurring diameter for spherical particles and the most frequently occurring largest diameter for the non-spherical particles in a particle size distribution histogram.

The first or second reactants useful in the practice of this invention can be incorporated into the compartments of individual porous organic or inorganic polymeric particles for example, by incorporating them in a first water phase to form a water-in-oil emulsion. In a particular embodiment, a first reactant can be incorporated into the first aqueous phase in the form of a milled solid particle dispersions of the reactant. Preparation of milled solid particle dispersions can include combining the reactant particles to be reduced in size with a dispersant and a liquid medium such as water or ethyl acetate in which the reactant particles are to be dispersed, in a suitable grinding mill in which the reactant particles are reduced in size and dispersed. The dispersant, an important ingredient in the milling, can be chosen to allow the reactant particles to be milled down in the liquid medium to a size small enough for incorporation into the compartments of the porous particles and alternatively, for the final indicator composition in which it is used. The dispersants can be selected to obtain efficient reactant particle size reduction during milling, provide good colloidal stability of the polymeric particles to prevent agglomeration after milling and impart the desired properties of the final indicator composition containing the reactant particles and the organic or inorganic polymeric particles containing the reactant particles.

The discrete compartments in the porous inorganic or organic polymeric particles can also comprise pore stabilizing materials such as hydrocolloids that are described below. In most instances, the same pore stabilizing material is used throughout the porous inorganic or organic polymeric particles.

The polymeric particles can be spherical or non-spherical depending upon the desired use. In a method used to prepare the organic polymeric particles, additives (shape control agents) can be incorporated into the first or second aqueous phases, in the oil (organic) phase to modify the shape, aspect ratio or morphology of the organic polymeric particles. The shape control agents can be added after or prior to forming the water-in-oil-in-water emulsion. In either case, the interface at the oil and second water phase is modified before solvent is removed, resulting in a reduction in sphericity of the polymeric particles. The porous inorganic or organic polymeric particles used in the present invention can also comprise surface stabilizing agents, such as colloidal silica, on the outer surface of each particle, in an amount of at least 0.1 weight %, based on the total dry weight of the particle.

The porous organic and inorganic polymeric particles can be provided as powders, or as aqueous suspensions (including water or water with water-miscible organic solvents such as alcohols). Such aqueous suspensions can also include surfactants or suspending agents to keep the particles suspended. The other compositional features are described in the following description of methods for preparing the porous organic and inorganic polymeric particles.

Methods for Making Porous Inorganic Polymeric Particles

In some embodiments, the first polymeric particle is composed of one or more first inorganic polymers (as described below). For example, the inorganic polymer can be a silicon-based or silicon-containing polymer. The silicon-containing polymer of the particle can be formed by hydrolysis and condensation of one or more inorganic gel precursors, including but not limited to, a substituted or unsubstituted metal alkoxide, such as substituted alkoxides having one or more alkyl, aryl, aminoalkyl, aminoaryl, glycidoxyalkyl, or glycidoxyaryl substituents, or mixtures thereof. Typically, the silicon gel precursor is a silicon alkoxide or a silicon alkyl alkoxide. The gel precursor can be a metal oxide gel precursor, silicon oxide gel precursor, or transition metal oxide precursor. The identity of the gel precursor chosen that is, whether a silicon oxide gel precursor or a particular metal oxide gel precursor chosen for use in a process, will depend on the intended use of the inorganic porous particles and, in particular, the suitability of the final product resulting from the condensation of the gel precursor for the intended use of the porous particles. The gel precursor is typically a silicon-based gel precursor, an aluminum-based gel precursor, a titanium dioxide-based gel precursor, an iron oxide based gel precursor, a zirconium dioxide-based gel precursor, or any combination thereof. A functionalized, derivatized or partially hydrolyzed gel precursor can be used.

There is a long list of potential silicon precursors that for convenience can be divided into 4 categories: silicates (silicon acetate, silicic acid, and salts thereof), silsequioxanes and poly-silsequioxanes, silicon alkoxides [from silicon methoxide (C1) to silicon octadecyloxide (C18)], and functionalized alkoxides (such as ethyltrimethoxysilane, aminopropyltriethoxy-silane, vinyltrimethoxysilane, diethyldiethoxysilane, and diphenyldiethoxy-silane). Further specific examples of silica-based gel precursors include tetramethoxysilane (TMOS), tetraethoxysilane (TEOS), tetrabutoxysilane (TBOS), tetrapropoxysilane (TPOS), polydiethoxysilane, methyltrimethoxysilane, methyltriethoxysilane, ethyltriethoxysilane, octylpolysilsesquioxane, and hexylpolysilsesquioxane.

Examples of aluminum-based gel precursors include aluminum ethoxide, aluminum n- or iso-propoxide, and aluminum n- or sec- or tert-butoxide. The alkoxide can also be modified using carboxylic acids (acetic, methacrylic, and 2-ethylhexanoic) or beta di-ketones such as acetylacetone, ethyl-acetylacetone, benzoylacetone, and other complexing agents.

Examples of titanium or zirconium gel precursors include alkoxides (such as ethoxide, propoxide, and butoxide), metal salts (such as chloride, oxychloride, sulfate, and nitrate), and acid and beta diketone complexes.

The silicon gel precursor or the metal oxide gel precursor can include from one to four alkoxide groups each having 1 or more oxygen atoms and 1 to 18 carbon atoms, more typically 1 to 5 carbon atoms. The alkoxide groups can be replaced by one or more suitable modifying groups or functionalized or derivatized by one or more suitable derivatizing groups (see K. Tsuru et al., *J. Material Sci. Mater. Medicine,* 1997, 8, which is incorporated herein by reference).

Typically, the silicon gel precursor is a silicon alkoxide or a silicon alkyl alkoxide.

Particular examples of suitable silicon alkoxide precursors include but are not limited to, methoxide, ethoxide, iso-propoxide, butoxide, and pentyl oxide. Particular examples of suitable silicon or metal alkyl (or phenyl) alkoxide precursors include but are not limited to, methyl trimethoxysilane, dimethyldimethoxysilane, ethyltriethoxysilane, diethyldiethoxysilane, triethylmethoxysilane, phenyltriethoxysilane, diphenyldiethoxysilane, and vinyltriethoxysilane. Alternatively, the silicon gel precursor can be a silicon carboxylate such as an acetate, tartrate, oxalate, lactate, propylate, formate, or citrate. Examples of other functional groups attached to silica gel precursors include esters, alkylamines, and amides.

Typically, the oxide gel precursor is an alkoxide that can be derivatized or functionalized. Typically, the transition metal oxide gel precursor is a transition metal alkoxide and the lanthanide metal oxide gel precursor is a lanthanide metal alkoxide. Examples of suitable metal oxide precursors include alkoxides such as methoxide, ethoxide, iso-propoxide, butyloxide, and pentyl oxide. Alternatively, the metal oxide gel precursor can be a metal carboxylate or a metal beta-diketonate, for example, an acetate, tartrate, oxalate, lactate, propylate, formate, citrate, or acetylacetonate. Examples of other functional groups attached to metal oxide precursors include esters, alkylamines, and amides. More than one type of metal ion or lanthanide ion can be present.

Particularly useful gel precursors are phenyltriethoxysilane, tetramethoxysilane and tetraethoxysilane. These compounds eventually form the inorganic metal oxide network forming the inorganic solid phase of the inorganic porous particles of this invention, which inorganic metal oxide network can be selected from alumina, silica, titania, zirconia, an organically-substituted metal oxide, and mixtures thereof. A particularly desirable inorganic oxide network comprises silicon. The inorganic gel precursors are present in the aqueous phase in an amount of at least 10 weight % and up to and including 70 weight %, and typically in an amount of at least 40 weight % and up to and including 60 weight %, based on the total aqueous phase weight. Mixtures of inorganic gel precursors can be used if desired to provide an inorganic oxide network comprising two or more different oxides.

Although hydrolysis of the metal alkoxide can occur without addition of an external catalyst, it is most rapid and complete when one is used. Therefore, an external catalyst can be present in the aqueous phase to increase the hydrolysis rate of the metal alkoxide precursor. The hydrolysis rate increases linearly with the concentration of $H^+$ or $H_3O^+$ ions in acidic media and with the concentration of $OH^-$ ion in basic medium.

Such catalysts are chosen based on the pH and ionic strength of the solution in which the hydrolysis and condensation can occur, which varies over a wide range, depending on the nature of the active material. However, the rate of hydrolysis and the rate condensation can vary according to the metal oxide precursor. Generally, the pH used in the hydrolysis and condensation process can range from 0 and up to and including 14, and is typically at least 1 and up to and including 11. When an acidic catalyst is used, the pH range is typically at least 1 and up to and including 6.5, or at least 1 and up to and including 4.5. When a basic catalyst is used, the pH range is typically at least 7 and up to and including 14 or at least 7 and up to and including 11. The pH at which the polycondensation (or condensation) is carried out is normally chosen so as to be at a value or within a certain pH range that does not substantially affect the activity of the active materials (which will depend on the nature of the active materials or the stability of the surfactant). One of ordinary skill in the art can determine optimal pH and ionic strength for particular gel precursors/active material combinations using the methods described herein. Useful catalysts in the aqueous phase are inorganic and organic acids or inorganic or organic bases, and include but are not limited to, hydrochloric acid, acetic acid, sodium hydroxide, potassium hydroxide, ammonium hydroxide, lower alkylamines, potassium fluoride, and hydrogen fluoride. Mixtures of catalysts can also be used if desired, particularly if different inorganic gel precursors are used that require different catalysts for solid network formation. An inorganic crosslinker can also be added to the continuous phase to preserve the mesoporous structure upon condensation. Examples of inorganic crosslinkers include, but are not limited to Zr-acetylacetonate and dibutyltindilaurate.

Further details for making these porous inorganic polymeric particles are provided in U.S. Pat. No. 8,394,396 (noted above).

Methods for Making Porous Organic Polymeric Particles

The details for preparing useful porous organic polymeric particles are provided in U.S. Patent Application Publications 2008/0176157 and 2010/0021838 and U.S. Pat. Nos. 7,754,409 and 8,100,628 (noted above).

The polymers (resins) used in the oil phase of the first emulsion can provide the solid continuous polymeric phase of the organic polymeric particles. Such polymers include but are not limited to, homopolymers and copolymers such as polyesters, styrenic polymers (for example polystyrene and polychlorostyrene), monoolefin polymers (for example, polymers formed from one or more of ethylene, propylene, butylene, and isoprene), vinyl ester polymers (for example, polymer formed from one or more of vinyl acetate, vinyl propionate, vinyl benzoate, and vinyl butyrate), polymers formed from one or more α-methylene aliphatic monocarboxylic acid esters (for example, polymers formed from one or more of methyl acrylate, ethyl acrylate, butyl acrylate, dodecyl acrylate, octyl acrylate, phenyl acrylate, methyl methacrylate, ethyl methacrylate, butyl methacrylate, and dodecyl methacrylate), vinyl ether polymers (such as polymers formed from one or more of vinyl methyl ether, vinyl ethyl ether, and vinyl butyl ether), and vinyl ketone polymers (for example, polymers formed from one or more of vinyl methyl ketone, vinyl hexyl ketone, and vinyl isopropenyl ketone). Particularly useful polymers include polystyrenes (including polymers of styrene derivatives), polyesters, styrene/alkyl acrylate copolymers, styrene/alkyl methacrylate copolymers, styrene/acrylonitrile copolymers, styrene/butadiene copolymers, styrene/maleic anhydride copolymers, polyethylene resins, and polypropylene resins. Other useful polymers include polyurethanes, urethane acrylic copolymers, epoxy resins, silicone resins, and polyamide resins. Still other useful polymers are polyesters of aromatic or aliphatic dicarboxylic acids with one or more aliphatic diols, such as polyesters of isophthalic or terephthalic or fumaric acid with diols such as ethylene glycol, cyclohexane dimethanol, and bisphenol adducts of ethylene or propylene oxides. The acid values (expressed as milligrams of potassium hydroxide per gram of resin) of the polyester resins are generally in the range of from 2 to 100. The polyesters can be saturated or unsaturated. Other useful polymers include polymers derived from cellulose such as cellulose acetate, cellulose acetate butyrate, and cellulose acetate propionate.

Methods for Using Indicator Compositions

The indicator compositions can be used in various ways to show or indicate a desired change as a result of a particular environmental condition stimulus, such as those described above. In simplest terms, the methods utilize exposing the indicator composition, in whatever way they are arranged in an article, to the given environmental condition stimulus to cause a detectable change in the indicator composition. Such detectable changes are described above, but the present invention is not limited to those detectable changes that are explicitly described. This exposure can be carried out using any desired set of conditions including desired time, temperature, pressure, pH, humidity, and chemical concentration.

For example, the method can comprise exposing the indicator composition to electromagnetic radiation, saturated steam, a dry heat at a temperature greater than 100° C., or pressure to cause a detectable change in the indicator composition. Examples of electromagnetic radiation include UV, visible, and infrared radiation, or combinations thereof. Saturated steam is a known material.

In other embodiments, the indicator composition can be exposed to a chemical or biological agent including but not limited to, ethylene oxide, a microbial agent, a viral agent, and a fungal agent. Thus, the chemical or biological agent (or condition) can be the environmental condition stimulus to be detected according to the present invention. As noted above, the change in the indicator composition can be a change in color or pH, or a combination thereof. For example, the indicator composition can be exposed to the environmental condition stimulus to cause a reaction of the second reactant with the first reactant to provide a color change. The indicator composition can be exposed to the environmental condition stimulus to cause a reaction of the first and second second reactants to provide the color change by the formation of insoluble metal sulfides.

In some embodiments, the method comprises exposing the indicator composition to the environmental condition stimulus to cause a reaction of the second reactant with the first reactant to provide a color change outside the first polymeric particle.

In still other embodiments, the method comprises exposing the indicator composition to the environmental condition stimulus to cause a reaction of the second reactant with the first reactant via an intermediate reaction product of either the first or second reactant. Examples of these embodiments include Examples of these embodiments include a first reactant that is a sulfur-containing compound that produces an intermediate reaction product of a sulfide ion, which reacts with a second reactant that is a metal salt.

The time for exposing the indicator composition can vary with the particular environmental condition stimulus to be detected, as well as the particular first and second reactants being used, but in many embodiments, the time for exposure can be at least 1 minute, or more than 1 minute and up to and including 60 minutes. For example, the method of this invention can include exposing the indicator composition for more than 1 minute to saturated steam or dry heat above 100° C. as the environmental condition stimulus.

In still other embodiments, the method comprises exposing the indicator composition to saturated steam, a dry heat temperature above 100° C., actinic (visible) radiation, ethylene oxide, or a combination thereof, to cause a reaction between the first reactant and the second reactant.

The present invention provides at least the following embodiments and combinations thereof, but other combinations of features are considered to be within the present invention as a skilled artisan would appreciate from the teaching of this disclosure:

1. A method for indicating an environmental condition stimulus, the method comprising:

exposing an indicator composition to an environmental condition stimulus to cause a detectable change in the indicator composition, the indicator composition comprising:

a) a first polymeric particle comprising a solid continuous polymeric phase and a first reactant, the first polymeric particle having a mode particle size equal to or less than 50 µm; and b) a second reactant outside of the first polymeric particle, which second reactant is capable of reacting with the first reactant when exposed to an environmental condition stimulus.

2. The method of embodiment 1, comprising:

exposing the indicator composition to electromagnetic radiation, saturated steam, dry heat greater than 100° C., ethylene oxide, formaldehyde, or any combination of these environmental condition stimuli, sufficient to cause a detectable change in the indicator composition.

3. The method of embodiment 1 or 2, comprising:

exposing the indicator composition to a chemical or biological agent sufficient to cause a detectable change in the indicator composition.

4. The method of embodiment 1 or 2, comprising exposing the indicator composition for more than 1 minute to saturated steam or dry heat above 100° C. as the environmental condition stimulus.

5. The method of any of embodiments 1 to 4, comprising exposing the indicator composition to the environmental condition stimulus sufficient to cause a detectable color change in the indicator composition, which detectable color change is a change from a colorless state to a colored state, from a colored state to a colorless state, or from one color hue to another color hue.

6. The method of any of embodiments 1 to 3 and 5, comprising exposing the indicator composition to ethylene oxide as the environmental condition stimulus.

7. The method of any of embodiments 1 to 6, comprising exposing the indicator composition to the environmental condition stimulus sufficient to provide the color change by the formation of insoluble metal sulfides.

8. The method of any of embodiments 1 to 7, wherein the first reactant is a source of a sulfide and the second reactant is reactive with the sulfide.

9. The method of any of embodiments 1 to 8, comprising exposing the indicator composition to the environmental condition stimulus sufficient to cause a reaction of the second reactant with the first reactant to provide a color change outside the first polymeric particle.

10. The method of any of embodiments 1 to 9, comprising exposing the indicator composition to the environmental condition stimulus to cause a reaction of the second reactant with the first reactant via an intermediate reaction product of either the first or second reactant.

11. The method of any of embodiments 1 to 10, comprising exposing the indicator composition to the environmental condition stimulus to cause a change in color in the indicator composition, which change in color is accomplished by hiding the original color of the indicator composition.

12. The method of any of embodiments 1 to 11, wherein the first polymeric particle further comprises one or more discrete compartments dispersed within the solid continuous polymeric phase.

13. The method of embodiment 12, wherein the first reactant is predominantly within the volume of the discrete compartments.

14. The method of any of embodiments 1 to 13, wherein the first polymeric particle has a mode particle size of at least 1 μm and up to and including 20 μm, and the indicator composition further comprises an organic polymeric matrix in which one or more of the first polymeric particles are dispersed.

15. The method of any of embodiments 1 to 14, wherein the second reactant is present in a second polymeric particle in the indicator composition.

16. The method of any of embodiments 1 to 15, wherein the first polymeric particle further comprises an inert colorant.

17. The method of any of embodiments 1 to 16, wherein the solid continuous polymeric phase of the first polymeric particle comprises one or more organic polymers.

18. The method of any of embodiments 1 to 16, wherein the solid continuous polymeric phase of the first polymeric particle comprises one or more inorganic polymers.

19. The method of any of embodiments 1 to 18, wherein the indicator composition further comprises an organic polymeric matrix.

20. The method of any of embodiments 1 to 19, for sterilizing surgical instruments or clothing, wherein the indicator composition is present in a pouch containing the surgical instruments or clothing, or the indicator composition is present as a label or free standing web in the pouch.

The following Examples are provided to illustrate the practice of this invention and are not meant to be limiting in any manner. The following materials were used in the Examples:

Carboxy methylcellulose, MW 250K (CMC), was obtained from Acros Organics or from Ashland Aqualon as Aqualon 9M31F.

NALCO 1060™ colloidal silica was obtained from Nalco Chemical Company as a 50 weight % aqueous dispersion.

The polyester resin Kao N was obtained from Kao Specialties Americas LLC, a part of Kao Corporation (Japan).

Eastman AQ™ 55S is a water dispersion of a sulfopolyester having a $T_g$ of 51-54° C. at 33.2 weight % solids.

Luviskol® K30 poly(vinyl pyrrolidone) from BASF.

Polypropylene/polyester bilayer film is a laminate of polyethylene terephthalate (PET) and polypropylene.

Paper represents a Kraft 60 g/m² medical grade paper.

Reactive Ink A was a light green copper carbonate {$CuCO_3.Cu(OH)_2$ (malachite)} aqueous dispersion and was obtained from Tempil.

Activator Ink Part B was a pink mixture consisting of barium thiosulfate hydrate $BaS_2O_3.H_2O$, elemental sulfur, and Pigment Violet 19 (PV 19, for pink color) also obtained from Tempil.

Reactive Ink A and the Activator Ink Part B together form a Class 1 steam sterilization indicator ink system that upon steam sterilization yields dark copper sulfide (CuS) that covers up the pink color of the inert colorant PV 19 to give an apparent pink to black color change.

Disperbyk® 190 is an aqueous solution of a dispersant from Byk Gardner.

Pigment Violet 19 13-7012 Hostaperm Red™ E5B-02 is a pigment obtained from Clariant Corporation.

Elemental sulfur powder, 325 mesh, was obtained from Alfa Aesar Corporation.

Zinc sulfide (ZnS) powder, less than 10 μm was obtained from Sigma Aldrich Corporation.

Solsperse® 32000 and Solsperse® 17000 are dispersants obtained from Lubrizol Corporation.

Triethoxyphenylsilane and tetramethyl orthosilicate were obtained from Sigma Aldrich Corporation.

GP-215 is a polyoxyethylene/polyoxypropylene silicone polyol from Genesee Polymer Company.

Dibutyltin dilaurate was obtained from Sigma Aldrich Corporation.

Airvol® C203 is a poly(vinyl alcohol) obtained from Airvol Corporation.

Neorez™ R-9330 is an aliphatic, nonionic polyester urethane film forming matrix polymer dispersion obtained from DSM NeoResins Inc. at 40 weight % solids.

Zonyl® FSN is a nonionic fluorinated surfactant obtained from DuPont and diluted with water to 1 weight % solids.

DSX® 1514 is a polyurethane thickener for rheology control of polymer latex coatings obtained from Cognis and diluted with water to 10 weight % solids.

Preparation of Milled Activator Ink B-1:

Activator Ink Part B (pink, 100 g, 21.05 weight % solids, batch 1), 10.6 g of a 37.9 weight % aqueous solution of Disperbyk® 190 dispersant, 1 g of nanopure water, and 200 ml of 1.8 mm zirconium oxide milling beads were added to a 16 oz glass jar. The jar and its contents were placed on a SWECO vibratory mill for 2 days. After milling, the dispersion was separated from the milling beads. The final dispersion after concentrating the ink by decanting off the supernatant, contained 52.7 weight % of Activator Ink B-2. Examination by optical microscopy showed that all particles were less than 1 μm in size.

Preparation of Milled Activator Ink B-2:

Activator Ink Part B (pink, 306.37 g, 48.96 weight % solids, batch 2), 56.68 g of a 37.9 weight % aqueous solution of Disperbyk® 190 dispersant, 236.95 g of nanopure water, and 600 g of 0.5 mm zirconium silicate milling beads were added to a 3 liter stainless steel kettle with a diameter of 140 mm and a chilled water jacket. The dispersion was stirred with a 60 mm diameter Cowles blade at a speed of 1000 rpm for 9.5 hours. After milling, the dispersion was separated from the milling beads. The final dispersion after concentrating the ink by decanting off the supernatant, contained 20.9 weight % of Activator Ink B-2. Examination by optical microscopy showed that all particles were less than 1 μm in size.

Preparation of Milled Activator Ink B-3:

A solid particle dispersion of elemental sulfur was prepared by combining 25 g of elemental sulfur powder, 9.45 g of a 37.9 weight % aqueous solution of Disperbyk® 190 dispersant, 65.55 g of nanopure water, and 250 ml of 2 mm zirconium oxide beads in a 16 oz glass jar. The glass jar was milled for 5 days on a SWECO® vibratory mill. After milling, the dispersion was separated from the beads. The final dispersion contained 24.43 weight % of elemental sulfur powder. Examination by optical microscopy showed that all particles were less than 1 μm in size.

Preparation of Milled Activator Ink B-4:

A solid particle dispersion of zinc sulfide was prepared by combining 20 g of zinc sulfide powder, 10.08 g of a 37.9 weight % aqueous solution of Disperbyk® 190 dispersant, 19.92 g of nanopure water, and 125 ml of 2 mm zirconium oxide beads in an 8 oz glass jar. The glass jar was rolled at a speed of 70 ft/min (6.5 m/min) for 4 days on a roller mill. After milling, the dispersion was separated from the beads. The final dispersion contained 38.0 weight % zinc sulfide. Examination by optical microscopy showed that all particles were less than 1 μM in size.

Preparation of Milled Reactive Ink A-1:

Reactive Ink Part A (green, 100 g, 26.42% solids, batch 1), 13.3 g of a 37.9 weight % aqueous solution of Disperbyk® 190 dispersant, 20 g of nanopure water, and 200 ml of 1.8 mm zirconium oxide milling beads were added to a 16 oz glass jar.

This jar was placed on a SWECO vibratory mill for 2 days. After milling the dispersion was separated from the milling beads. The final dispersion contained 19.29 weight % of Reactive Ink A-1. Examination by optical microscopy showed that all particles were less than 1 µm in size.

Preparation of Milled Reactive Ink A-2:

Reactive Ink Part A (green, 907 g, 30.19 weight % solids, batch 2), 103.46 g of a 37.9 weight % aqueous solution of Disperbyk® 190 dispersant, 358.66 g of nanopure water, and 1506 g of 500 mm crosslinked poly(styrene-co-divinylbenzene) milling beads were added to a 5 liter stainless steel kettle with a diameter of 178 mm and a chilled water jacket. The dispersion was stirred with a 60 mm diameter Cowles blade at a speed of 1000 rpm for 21 hours. After milling, the dispersion was separated from the milling beads. The final dispersion contained 18.24 weight % of Reactive Ink A-2. Examination by optical microscopy showed that all particles were less than 1 µm.

Preparation of Milled Reactive Ink A-3:

Reactive Ink Part A (green, 109.6 g, 30.19 weight % solids), 12.5 g of a 37.9 weight % aqueous solution of Disperbyk® 190 dispersant and 134 g of 500 mm crosslinked poly(styrene-co-divinylbenzene) milling beads were added to a 0.5 liter stainless steel kettle with a diameter of 80 mm and a chilled water jacket. The dispersion was stirred with a 40 mm diameter Cowles blade at a speed of 2400 rpm for 7 hours. After milling, the dispersion was separated from the milling beads. The final dispersion contained 13.16 weight % of Reactive Ink A-3. Examination by optical microscopy showed that all particles were less than 1 µm in size.

Preparation of Pigment Violet Dispersion PD-1 (Ethyl Acetate):

Pigment Violet 19 13-7012 Hostaperm Red™ E5B-02 (20 g), 13.33 g of a 30 weight % solution of Solsperse® 32000 dispersant in ethyl acetate, 66.67 g of ethyl acetate, and 250 ml of 1.8 mm zirconium oxide milling beads were added to a 16 oz glass jar. The jar was placed on a SWECO vibratory mill for 4 days. After milling, the dispersion was separated from the milling beads. The final dispersion contained 7.69 weight % of Pigment Violet 19. Examination by optical microscopy showed that all particles were less than 1 µm in size.

Preparation of Pigment Violet Dispersion PD-2 (in Water):

Pigment Violet 19 13-7012 Hostaperm Red™ E5B-02 (20 g), 10.08 g of a 37.9 weight % aqueous solution of Disperbyk® 190 dispersant, 69.92 g of nanopure water, and 250 ml of 1.8 mm zirconium oxide milling beads were added to a 16 oz glass jar. The jar was placed on a SWECO vibratory mill for 4 days. After milling, the dispersion was separated from the milling beads. The final dispersion contained 13.24 weight % of Pigment Violet 19. Examination by optical microscopy showed that all particles were less than 1 µm in size.

Concentrated Reactive Ink A-1 was prepared from Reactive Ink A-1 described above by pipetting off the supernatant after settling, resulting in a final slurry at 31.25 weight % of Reactive Ink A-1.

Porous Organic Polymer Particle Preparation and Characterization:

One or more indicator composition components (reactants) can be isolated from other components by encapsulating one or more reactants within discrete compartments in polymeric particles that can be formed by water-in-oil-in-water double emulsions.

A very fine water-in-oil emulsion was prepared from an oil phase made up of ethyl acetate in which the encapsulating polymer is dissolved, and a first water phase containing the reactant(s) to be encapsulated and a dissolved hydrocolloid to stabilize the emulsion. In the examples below, an aqueous solution of carboxy methyl cellulose (CMC) was used as the hydrocolloid and the oil phase comprised a 20 weight % solution of Kao N resin in ethyl acetate. More than one of these emulsions can be prepared using different reactants to isolate them in different pores within the same porous polymeric particle. The emulsion was prepared by mixing the water and oil phases for one minute at 6800 RPM using a Silverson L4R homogenizer (Silverson Machines Inc.). The resulting water-in-oil emulsion was further homogenized by passing it twice through a Microfluidizer® Model #110T (Microfluidics) at a pressure of 8900 psi.

Aliquots of each resulting very fine water-in-oil emulsions containing the chosen indicator composition components were dispersed in a second water phase containing colloidal silica stabilizer and a pH buffer at a controlled ionic strength using the Silverson homogenizer for two minutes at 2800 RPM followed by homogenization in an orifice homogenizer at 1000 psi to form a water-in-oil-in-water emulsion. In the examples below, NALCO™ 1060 in a 200 mmolar, pH 4 citrate-phosphate buffer was used as the second water phase.

Porous polymeric particles were obtained by evaporating the ethyl acetate from the water-in-oil-in-water emulsion droplets using a Heidolph Laborata rotary evaporator at 40° C. under reduced pressure and filtering the resulting suspension of porous polymeric particles containing the encapsulated indicator composition reactant(s) using a glass fitted funnel. The porous polymeric particles were washed multiple times by re-suspending them in water and filtering using a glass flitted funnel. In some instances repeated washing and centrifugation at 5000 rpm were used to clean the particles.

The final filter cake solids concentration was measured on a CEM LabWave 9000 Microwave Moisture/Solids Analyzer and the mode particle size was measured using a Sysmex FPIA3000.

Print Sample Preparation:

Test samples of each indicator composition were printed on Kraft 60 g/m² medical grade paper using a Harper Scientific Phantom Proofer with a 100 lip ceramic Anilox roller. Each print was cut into 2 inch (5.1 cm) strips and sealed with a polypropylene/polyester bilayer film. Each sample was then treated at various times in an A-Dec® W&H® Lisa BM-17 Water Steam Sterilizer run at either the 135° C. or 121° C. sterilization cycle and stopped manually when temperatures of 121° C., 129.4° C., and 135° C. were reached, or after reaching 2 minutes, 4 or 5 minutes, 10 minutes, and 18 minutes at 135° C., and after reaching 2 minutes, 6 minutes, 12 minutes, 20 minutes, and 30 minutes at 121° C. This particular model of steam sterilizer takes between 5 and 8 minutes to the sterilization cycle to reach the 135° C. after starting the final ramp of temperature and pressure. As such, the indicator changes color during the long and variable ramp from 100° C. to desired sterilization condition. The indicator components reacted to create a color change as expected by those skilled in chemistry with a rate that doubled for every 10° C. increase in temperature. To remove the effects of the long and variable temperature ramp, the time was recorded at every 2.8° C. (5° F.) once above 110° C. and at the manual stop. The effective time at 135° C. was estimated by numerically integrating two to the power of the difference the recorded temperature and 135° C. divided by 10:

$$t_{eff} = \int 2^{(T(\tau)-135)/10} dt$$

Each sample was removed upon unlocking the door (approximately 2 minutes and 20 seconds after manual stop) and excess water was dried from the sample.

Metrics Used to Evaluate Response of Print Samples to Steam Sterilization:

An advantage achieved by the present invention is providing the ability to slow down the rate of color change of a Class 1 indicator system (reaction between Reactive Ink A and Activator Ink B) enabling it to perform as a Class 5 indicator by responding to the three critical parameters: time, temperature, and the presence of saturated steam. The metrics used to measure the change before and after sterilization are $\Delta D_c$ (change in cyan status A density) to measure the rate of the reaction, and $L^*$, $a^*$, $b^*$, $\Delta E$, and $\Delta h$ (change in CIELab hue angle) to reflect the perceived color change. The rate of color change is proportional to the inverse of the time constant $\tau$ and was calculated for each of the metrics described above.

Color change was evaluated by measuring CIELab values using a GreytagMacbeth™ Spectrolino with settings of D65 light source simulation and a viewing angle of 2 degrees of stenciled areas for both unprinted and printed regions measured before sealing with the polypropylene/polyester bilayer film and after subjecting to the steam treatment and after removal of the film. The $L^*$, $a^*$ and $b^*$ values were measured and $\Delta E$ and $\Delta h$ computed. The term $\Delta h$ is the change in the CIELab hue angle in degrees and the term $\Delta E$ measures the magnitude of visible change in the Lab color space. A "Least-Squares" exponential fit of $L^*$, $\Delta E$ and $\Delta h$ to the effective time at 135° C. was performed to obtain the level of change $\Delta$ and the time constant $\tau$. In all cases, the rate of change can be expressed as a time constant $\tau$ for an exponential decay from the starting color to the final endpoint color for a total possible color change of $\Delta$. The results are presented in TABLE I below.

Comparative Example 1

An indicator composition outside of the scope of this invention was prepared by mixing 4.330 g of a Reactive Ink A2, 3.542 g of Activator Ink B2 containing 20.9 weight % solids, 0.148 g of Zonyl® FSN nonionic surfactant, and 2.059 g of distilled water. The resulting indicator composition contained 22 weight % of Reactive Ink A and 7.3 weight % of Activator Ink B. This ink was printed and evaluated as described above and the results are presented in the TABLE I below.

Comparative Example 2

Effect of Organic Matrix Polymer

A second indicator composition outside of the scope of this invention having an organic matrix polymer was prepared by mixing 4.295 g of Reactive Ink A2 as in Comparative Example 1, 3.515 g of Activator Ink B2 as in Comparative Example 1, 1.306 g Neorez™ R-9330, 0.148 g of Zonyl® FSN nonionic surfactant, and 0.95 g of distilled water. The resulting indicator composition was printed and evaluated as described above and the results are presented in the TABLE I below. Comparative Example 2 compared to Comparative Example 1 demonstrates that a relatively low level of organic matrix polymer can increase the rate of color change in the indicator composition.

Comparative Example 3

Effect of an Inert Colorant

Another indicator composition outside of the scope of this invention was prepared with an organic matrix polymer and additional inert colorant by mixing 4.313 g of Reactive Ink A2 as in comparative Example 1, 3.502 g of Activator Ink B2 as in comparative Example 1, 1.334 g Neorez™ R-9330, 0.154 g of Zonyl® FSN nonionic surfactant, 0.12 g of PD-2, and 0.792 g of distilled water. The resulting indicator composition was printed and evaluated as described above and the results are presented in the TABLE I below. Comparative Example 3 demonstrates that additional inert colorant had a low impact on slowing the rate of color change compared to Comparative Example 1.

Invention Example 1

Preparation of Porous Organic Polymeric Particles Having Discrete Compartments Containing Activator Ink B-2

Porous organic polymeric particles containing 18 weight % Activator Ink B-2 in the compartments and a mode particle size of 3 μm were prepared as described above, 52.3 g of Activator Ink B-2, using 32 g of a 5 weight % aqueous solution of CMC as and 239.5 g of a 16.5 weight % solution of Kao N polymer resin to form the first emulsion. A 250 g aliquot of the resulting emulsion was dispersed in 416.7 g of the second water phase comprising a 300 millimolar pH 4 citrate-phosphate buffer and 25.0 g of NALCO™ 1060 and converted to porous polymeric particles as described above.

An indicator composition of this invention was prepared using 0.996 g of Concentrated Reactive Ink A-1 mixed with 1.508 g of the 3 μm porous polymeric particles containing Activator Ink B-2 at 34.9 weight % solids and 0.283 g of distilled water. The resulting indicator composition contained 11 weight % Reactive Ink A and 3.4 weight % Activator Ink B. This indicator composition was printed, treated, and analyzed as described above except that the resulting prints were placed in an oven at about 100° C. for 1 minute to adhere the polymeric particles to the paper. The results presented in TABLE I below show that encapsulating the activator component (first reactant) within a porous polymeric particle slowed the chemical reaction with the second reactant by about a factor of 2 compared to the Comparative Example 1 for $L^*$ and $\Delta E$. The hue angle did not reflect that change due to the small amount of inert colorant in the particles. Because the amount of Reactive ink $\Delta$ was less than the Comparative Example 1, less total color change $\Delta$ was seen for $L^*$ and $\Delta E$.

Invention Example 2

Low Level of Inert Colorant and Porous Organic Polymeric Particles Having Discrete Compartments Containing Activator Ink B-2

An indicator composition useful in this invention comprising 1.589 g of concentrated Reactive Ink A-1, 2.619 g of the 3 μm particles described in Invention Example 1, 0.414 g of Neorez™ R-9330, 0.413 g of DSX® 1514, 0.245 g of PD-2 described above diluted 1:9 in water, 0.069 g of Zonyl® FSN nonionic surfactant, and 0.458 g of distilled water was prepared and printed for evaluation. The low level of organic matrix polymer Neorez™ R-9330 used in this example was sufficient to adhere the porous polymeric particles to the Kraft medical grade paper without resorting to heating in an oven. The results presented in TABLE I below show that a low level of inert colorant can be added to the indicator composition to slow the change in hue angle. Additionally, the $L^*$ and $\Delta E$ values showed a slower change than was observed in Invention Example 1.

Invention Example 3

Low level of Inert Colorant in the Solid Continuous Polymer Phase of the Porous Organic Polymeric Particles Having Discrete Compartments Containing Activator Ink B-2

Porous organic polymeric particles with a mode particle size of 3 μm were made as described in Invention Example 1, except that 236.9 g of a 16.6 weight % solution of Kao N polymer resin and 2.6 g of a pigment dispersion similar to PD-1 containing 9.5 weight % PV19 were used in the oil phase. The resulting porous polymeric particles contained 18 weight % activator ink B solids in the compartments and 0.5 weight % PV19 in the solid continuous polymer phase of polymeric particles.

An indicator composition useful in this invention was prepared using 2.034 g of Concentrated Reactive Ink A-1 mixed with 3.149 g of the 3 μm porous polymeric particles containing Activator Ink B-2 in the compartment and 0.5 percent PV19 in the continuous polymer phase at 37.3 weight % solids, 0.522 g of Neorez™ R-9330, 0.438 g of DSX® 1514, 0.065 g of Zonyl® FSN nonionic surfactant, and 1.02 g of distilled water. The resulting indicator composition contained 11 weight % Reactive Ink A and 3.4 weight % Activator Ink B. This indicator composition was printed, treated, and analyzed as described above. The results are presented in TABLE I below for Invention Example 3 showing equivalent performance as Invention Example 2 but with 50% more inert colorant than in Invention Example 2. This is due to the reduction in covering power of the insert colorant when confined to the polymeric particles. Thus the presence of extra inert colorant confined to the particle or in the coating fluid delays the change in hue angle.

Invention Example 4

Medium Amount of Inert Colorant in Solid Continuous Polymer Phase of the Porous Organic Polymeric Particles Having Discrete Compartments Containing Activator Ink B-2

Porous organic polymeric particles with a mode particle size of 3 μm were made as in Invention Example 1 except that 53.6 g of Activator Ink B-2 was used along with 12 g of a 10 weight % solution of CMC and 3.8 g of distilled water for the first water phase, and 183.6 g of a 20 weight % solution of Kao N polymer resin in ethyl acetate and 8.0 g of Pigment Dispersion PD-1 for the oil phase. A 185 g aliquot of the resulting water-in-oil emulsion was dispersed in 308.3 g of the second water phase comprising a 300 mmol pH 4 citrate-phosphate buffer and 19.4 g of NALCO™ 1060. Irregular shaped colored porous polymeric particles were obtained at 40 weight % solids and contained 20 weight % activator ink B solids in the compartments and 1.5 weight % PV 19 in the solid continuous polymer phase of polymeric particles.

An indicator composition useful in this invention prepared using 0.821 g of concentrated Reactive Ink A-1, 1.076 g of these porous polymeric particles and 0.468 g of distilled water was printed for evaluation as described above. The resulting indicator composition contained 10 weight % Reactive Ink A and 3.6 weight % Activator Ink B. This indicator composition was printed, treated, and analyzed as described above. The results are presented in TABLE I below showing a greater slowing of hue angle compared to that observed in Invention Example 3.

Invention Example 5

High Amount of Inert Colorant in the Solid Continuous Polymer Phase of the Porous Organic Polymeric Particles Having Discrete Compartments Containing Activator Ink B-2

Porous organic polymeric particles with a mode particle size of 3 μm was made as in Invention Example 1 except that 220.0 g of a 17.2 weight % solution of Kao N polymer resin and 19.5 g of pigment dispersion PD-1 were used in making the first emulsion. The resulting particles contained 18 weight % activator ink B solids in the compartments of the particles and 3 weight % PV 19 in the solid continuous polymer phase.

An indicator composition useful in this invention was prepared using 1.598 g of concentrated Reactive Ink A-1, 2.922 g of the colored porous polymeric particles containing Activator Ink B-2 in the compartment and with 3 weight % PV 19 in the continuous polymer phase at 31.9 weight % solids, 0.396 g of Neorez™ R-9330, 0.412 g of DSX® 1514, 0.064 g of Zonyl® FSN nonionic surfactant, and 0.6 g of distilled water and was printed for evaluation as described above. The resulting indicator composition contained 8.3 weight % Reactive Ink A and 2.8 weight % Activator Ink B. This indicator composition was printed, treated, and analyzed as described above. The results presented in TABLE I below showed a greater slowing of color change of Invention Example 5 for hue angle compared to that observed for Invention Example 4.

Invention Examples 1-5 demonstrate that the inert colorant level can be used as one factor to modify the timing or duration of the color change from reaction of the first and second reactants in the indicator compositions.

Invention Example 6

Effect of Particle Size of Porous Organic Polymeric Particles Having Discrete Compartments Containing Activator Ink B-2

Porous organic polymeric particles were prepared as described in Invention Example 1 except that 25.0 g of NALCO 1060 was used. The resulting porous polymeric particles containing 18 weight % Activator Ink B-2 in the compartments were nearly spherical and had a mode particle size of 7 μm.

An indicator composition useful in this invention comprising 2.051 g of concentrated Reactive Ink A-1, 3.462 g of the 7 μm polymer particles, and 0.508 g of distilled water was prepared and printed for evaluation. The resulting indicator composition contained 10.6 weight % Reactive Ink A and 3.3 weight % Activator Ink B. This indicator composition was printed, treated, and analyzed as described above except that the resulting prints were placed in an oven at about 100° C. for 1 minute to adhere the porous polymeric particles to the paper. The results presented in TABLE I below show that the rate of change in $L^*$ and $\Delta E$ was further slowed compared to that observed in Invention Example 1. However, the rate of change for hue angle due was greater than that observed in Example 1 due to the reduction of covering power of the inert colorant when it was encapsulated in the compartments of the larger porous polymeric particles. This shows that the size of the porous polymeric particles is another way to control or modify the rate of formation of the dark metal sulfide from reaction of first and second reactants.

Invention Example 7

Effect of Discrete Compartment Size in Porous Organic Polymeric Particles Containing Activator Ink B-2

Porous organic polymeric particles with larger compartment size were prepared as described in Example 1 except that the water-in-oil-in-water emulsion used to make the porous organic polymeric particles used in Invention Example 1 was diluted with equal parts water before evaporation of ethyl acetate. The resulting porous organic polymeric particles had an increased compartment size as observed with microscopy and contained 18 weight % of Activator Ink B-2 and had a mode particle size of 3.5 µm.

An indicator composition useful in the present invention similar to that of Invention Example 2 comprising 1.604 g of concentrated Reactive Ink A-1, 3.404 g of these porous organic polymeric particles containing Activator Ink B-2 at 26.84 weight % solids, 0.416 g of Neorez™ R-933, 0.419 g of DSX® 1514, 0.247 g of PD-2 diluted 1:9 in water, and 0.071 g of Zonyl® FSN nonionic surfactant was prepared and printed for evaluation. The resulting indicator composition contained 8.1 weight % of Reactive Ink A and 2.7 weight % of Activator Ink B. Table I below shows that increasing the compartment size of the porous polymeric particles used in Invention Example 7 did not slow the color change as much as was observed in Invention Example 2 as seen by the rate of change in L*, ΔE, and Δh. This result is attributed to thinning of the solid continuous polymer phase of the porous polymeric particles upon increasing the compartment size using the procedure described above. The polymeric barrier provided by the compartment walls is smaller than that used in Invention Example 2 and thus the reaction forming the dark metal sulfide from reaction of first and second reactants proceeded at a faster rate.

Invention Example 8

Effect of Using Elemental Sulfur Alone as First Reactant in Porous Organic Polymeric Particles Having Discrete Compartments Containing Activator Ink B-3

Porous organic polymeric particles with a mode particle size of 4 µm were prepared as described in Invention Example 5 except that 40.9 g of Activator Ink B-3 and 11.9 g of water were used in place of Activator Ink B-2. The resulting porous polymeric particles contained 20 weight % of elemental sulfur as the first reactant in the compartments and 3 weight % of PV 19 in the solid continuous polymer phase of porous polymeric particles.

An indicator composition useful in this invention was prepared using 2.535 g of concentrated Reactive Ink A-1, 2.021 g of these porous polymeric particles 28.1 weight % solids 0.443 g of Neorez™ R-9330, 0.417 g of DSX™ 1514, 0.071 g of Zonyl® FSN nonionic surfactant, and 1.006 g of distilled water and was printed for evaluation as described above. The resulting indicator composition contained 12.2 weight % of Reactive Ink A and 2.2 weight % of elemental sulfur. This indicator composition was printed, treated, and analyzed as described above. The results presented in TABLE I below show that compared to Comparative Example 3, the rate of color change was slower demonstrating the usefulness of the indicator composition in the present invention.

Invention Example 9

Effect of Using Elemental Sulfur with Zinc Sulfide in Porous Organic Polymeric Particles Having Discrete Compartments Containing Activator Ink B-3

An indicator composition useful in this invention was prepared using 2.531 g of concentrated Reactive Ink A-1, 1.531 g of the porous organic polymeric particles of Invention Example 8, 0.281 g of Activator Ink B-4, 0.406 g of Neorez™ R-9330, 0.413 g of DSX® 1514, 0.064 g of Zonyl® FSN nonionic surfactant, 0.352 g of PD-2 diluted 1:9 in water, and 0.89 g of distilled water, and the indicator composition was printed for evaluation as described above. The resulting indicator composition contained 12.2 weight % of Reactive Ink A, 1.65 weight % of elemental sulfur, and 1.65 weight % of zinc sulfide. The indicator composition was printed, treated, and analyzed as described above. The results presented in TABLE I below show that the presence of zinc sulfide does not impact the rate of color change significantly compared to Invention Example 8. However, it provides stability to the printed indicator composition as described below and shown in TABLE II.

Discussion of Results:

As described above, the rate of color change can be expressed in terms of a time constant τ and a total amount of change Δ as shown in the following TABLE I. The formation of dark copper sulfide lowers the lightness (negative values of Δ for L*) and changes the hue (measured by Δh). It was found that the change in hue was complete by 2 to 3 times τ (for Δh) while the corresponding L* value changed only by 15 to 20 for Comparative Examples 1 through 3. L* varied with printing lay down of the indicator composition, making its use unreliable after the hue reached a constant value. On the other hand, the hue was determined by the ratio of the reactants in the indicator composition (for example, the amount of inert pigment relative to the reactive ink components). Thus a Δ for L* of −15 to −20 is sufficient to provide a distinctive darkening provided that the time constant τ for Δh is nearly the same as that for L*.

TABLE I

| Parameter | L* Lightness Δ | L* Lightness τ | ΔE Δ | ΔE τ | Δh Hue Δ | Δh Hue τ |
|---|---|---|---|---|---|---|
| Comparative Example 1 | −39 | 141 | 41 | 109 | 116 | 31 |
| Comparative Example 2 | −36 | 111 | 39 | 84 | 112 | 20 |
| Comparative Example 3 | −32 | 115 | 40 | 74 | 114 | 47 |
| Invention Example 1 | −19 | 265 | 23 | 224 | 107 | 26 |
| Invention Example 2 | −20 | 322 | 28 | 305 | 100 | 115 |
| Invention Example 3 | −17 | 295 | 25 | 351 | 97 | 116 |
| Invention Example 4 | −19 | 389 | 27 | 310 | 94 | 270 |
| Invention Example 5 | −17 | 400 | 28 | 286 | 82 | 350 |
| Invention Example 6 | −19 | 403 | 25 | 395 | 97 | 16 |
| Invention Example 7 | −20 | 237 | 28 | 229 | 100 | 86 |
| Invention Example 8 | −23 | 344 | 31 | 247 | 94 | 170 |
| Invention Example 9 | −17 | 261 | 22 | 196 | 68 | 164 |

The data presented in TABLE I provide the following understanding. Invention Example 1 demonstrates that encapsulating the activator component (first reactant) in the compartments of the porous polymeric particles slowed the desired chemical reaction with the second reactant (that causes the color change through the formation of a metal sulfide) by more than a factor of 2 as can be seen by the increase in the time constant value, τ for L* and ΔE compared to Comparative Example 3. There are other contributions to the color change such as the presence and amount of inert colorants, for example PV 19. In Invention Example 1, the amount of PV 19 present in the indicator composition was less than that used in Comparative Example 3 by about a factor of 5 since it reflects only the inert colorant that was present in the Activator Ink Part B used to make the particles. As a result, the perception of color change as measured by Δh was faster for Invention Example 1 than that observed for Comparative Example 3.

In Invention Examples 2 through 5, the level and placement of an inert colorant were evaluated with the perception of color change as measured by Δh. Invention Example 2 demonstrated the use of a relatively low amount of PV19 (0.056 weight % of the ink) in the water of the indicator composition to slow the perception of color change by a factor of more than four for Invention Example 1 and more than twice for Comparative Example 3 as measured by Δh. Invention Example 3 demonstrated that an equivalent effect on Δh was achieved by increasing the amount of PV19 in the porous organic polymeric particles by the addition of 0.081 weight % PV 19 to the polymer walls of the porous organic polymeric particles. Invention Examples 4 and 5 demonstrated that the apparent color change by hue angle was further slowed by the addition of PV19 to the polymer walls of the porous organic polymer particles at 0.27 weight % and 0.47 weight %, respectively, of the indicator composition with little change in lightness or ΔE but a reddening of the final hue.

Invention Example 6 demonstrated the effect of the size of the porous organic polymeric particle on the rate of color change. The increased diffusion path of the activator component (first reactant) slowed the conversion of indicator composition to a dark color as compared to Invention Example 1. The rate of color change as measured by L* and ΔE was nearly inversely proportional to the size of the porous organic polymeric particle. However, there was a greater loss of the covering power for PV19 in the compartments for the larger porous polymeric particles and Δh changed more quickly.

Invention Example 7 demonstrated the effect of the compartment size in the porous organic polymeric particles on the rate of color change in the indicator composition. Increasing the compartment size by expanding the compartments resulted in thinner porous organic polymeric particle walls and reduced the diffusion path as compared to Invention Example 2, resulting in faster color change as measured with all three measured properties.

Invention Examples 8 and 9 demonstrated the use of different indicator composition components, for example a mixture of elemental sulfur and zinc sulfide as the first reactant. The rate of color change for these steam sterilizer indicator compositions was slower than for the indicator composition of Comparative Example 3, demonstrating the usefulness of the inventive indicator compositions. The use of zinc sulfide in Invention Example 9 provided stability to the printed indicator composition. The printed indicator compositions were subjected to a lab environment (ambient conditions) for 1 week followed by accelerated aging in vacuum of about 0.1 torr at room temperature. Indicator composition samples were periodically removed, sealed with a polypropylene/polyester bilayer film, and subjected to steam sterilization for an effective time or 3 minutes at 135° C., inducing a substantial color change in the non-aged indicator composition samples. The contribution of metal sulfide formation to the color change was evaluated using cyan density measurements (as described above).

The changes in cyan density due to sterilization for the aged indicator composition samples divided by the change in cyan density in the non-aged sample were compared for different aging conditions as shown in TABLE II. Invention Example 9 retained the most activity when subjected to this accelerated aging test. The indicator composition of Comparative Example 3 containing a much higher level of sulfur and the indicator composition of Invention Example 5, upon aging lost enough sulfur to cause formation of copper oxide instead of copper sulfide.

TABLE II

Aging Test Evaluations
Relative Cyan Density after Aging and
Sterilization for Effective Times at 135° C.

| | Comparative Example 3 | Invention Example 5 | Invention Example 9 |
|---|---|---|---|
| Effective time (minutes) | 3 | 7.5 | 3 |
| 1 Week (ambient conditions) | 87% | 68% | 92% |
| 1 Week + 1 Day under vacuum | 51% | 38% | 89% |
| 1 Week + 3 Days under vacuum | 33% | 28% | 85% |
| 1 Week + 7 Days under vacuum | 38% | 31% | 76% |

Preparation of Porous Inorganic Polymeric Particles P-1 Having Discrete Compartments Containing Activator Ink B-1 Using a Multiple Emulsion Process:

An oil phase was prepared by combining 23.04 g of tri-ethoxyphenylsilane, 0.48 g of GP-215, and 0.48 g of dibutyltin dilaurate. A first water-in-oil emulsion was prepared by dispersing 6.0 g of milled Activator Ink B-1 in the oil phase by sonication using a Cole Palmer 4710 Ultrasonic Homogenizer probe at 50 percent duty cycle for 20 seconds.

A water-in-oil-in-water emulsion ("second emulsion") was then prepared by dispersing the first water-in-oil emulsion in 270 g of a solution of 0.5 weight % of Airvol® C203 poly(vinyl alcohol) and 10 weight % of Nalco® 1060 silica in nanopure water using a Silverson homogenizer at 6000 rev/min for 1 minute. This water-in-oil-in-water emulsion was placed in a 30° C. water bath and stirred for 21 hours in order to cause gelling and to polymerize to form porous inorganic polymeric particles. After stirring, the particles were centrifuged at 7000 rpm and washed with nanopure water twice to remove excess poly(vinyl alcohol) and silica. The washed porous inorganic polymeric particles were dried in a vacuum oven at ambient temperature, and passed through a 100 pun mesh screen to produce a dry powder. The final dried porous inorganic polymeric particles were polydispersed, with a distribution ranging from 1 μm to about 10 μm and contained about 8.1 weight % encapsulated Activator Ink B-1 as the first reactant.

Reparation of Inorganic Polymeric Particles P-2 with Encapsulated Activator Ink B-1 Using a Single Emulsion Process A solution of hydrolyzed tetramethyl orthosilicate (TMOS) was prepared by combining 50 g of TMOS, 31.63 g of methanol and 23.75 g of 1N hydrochloric acid. The solution was stirred overnight to full hydrolysis, for further use in the aqueous phase of a water-in-oil emulsion.

An aqueous phase was prepared by adjusting 20 g of the hydrolyzed TMOS solution to a pH of 5.98 with 0.1N sodium hydroxide. After the pH adjustment, 4.92 g of milled Activator Ink B-1 were added to the TMOS solution with stirring to comprise the aqueous phase. An oil phase was prepared by combining 141.88 g of cyclohexane and 79.81 g of a 10 weight % solution of Solsperse 17000® in cyclohexane. A water-in-oil emulsion was then prepared by dispersing the aqueous phase in the oil phase using a Silverson homogenizer at 6000 rev/min for 2 minutes. The resulting water-in-oil emulsion was placed in a 30° C. water bath and stirred for 21 hours in order to cause gelling and to polymerize to form porous inorganic polymeric particles. After stirring, the particles were centrifuged at 7000 rpm and washed with ethanol twice to remove cyclohexane and surfactant. The washed inorganic polymeric particles were dried in a vacuum oven at 40° C. and passed through a 100 μm mesh screen to produce a dry powder. The final dried inorganic polymeric particles were polydispersed with a distribution ranging from 1 μm to about 7 μm and contained about 18.7 weight % encapsulated Activator Ink B-1 as the first reactant.

Invention Example 10

Preparation and Coating of Indicator Composition Using Particles P-1

An indicator composition useful in this invention was prepared by combining 4.56 g of Reactive Ink A-3 second reactant, 2.48 g of porous inorganic polymeric particles P-1 described above containing Activator Ink B-1 as the first reactant, 0.77 g of a 25.84 weight % aqueous solution of AQ55™, and 2.19 g of nanopure water. The resulting indicator composition was sonicated using a Cole Palmer 4710 Ultrasonic Homogenizer probe for 10 pulses at 50 percent duty cycle. The resulting indicator composition (MCB-I-1) was coated onto 90 g/m² Kraft medical grade paper using a 0.5 mil (1.3 mm) knife. The final dried laydown contained 0.25 g/m² of Activator Ink B-1 (first reactant) and 0.76 g/m² of Reactive Ink A-3 (second reactant).

Invention Example 11

Preparation and Coating of Indicator Composition Using Particles P-2

An indicator composition useful in this invention was prepared and coated in the same manner as Invention Example 10, except that it contained 1.07 g of porous inorganic polymeric particles P-2 and 3.6 g of nanopure water.

Comparative Example 4

An indicator composition outside of the scope of the present invention was prepared by combining 4.56 g of Reactive Ink A-3, 1.14 g of Activator Ink B-1, 0.77 g of a 25.84 weight % aqueous solution of AQ55™, and 3.52 g of nanopure water. The dispersion was sonicated using a Cole Palmer 4710 Ultrasonic Homogenizer probe for 10 pulses at 50 percent duty cycle. The resulting indicator composition (was coated onto 90 g/m² Kraft medical grade paper using a 0.5 mil (1.3 mm) knife. The final dried laydown contained 0.25 g/m² of Activator Ink B-1 and 0.76 g/m² of Reactive Ink A-3, which were the same amounts as in Invention Examples 10 and 11.

Comparative Example 5

An indicator composition outside of the present invention was prepared by combining 1.12 g of Reactive Ink Part A (30.16 weight % solids), 2.19 g of Activator Ink Part B (21.05 weight % solids), 0.77 g of a 25.84 weight % aqueous solution of AQ55™, and 5.91 g of nanopure water. The resulting dispersion was sonicated using a Cole Palmer 4710 Ultrasonic Homogenizer probe for 10 pulses at 50 percent duty cycle. The resulting indicator composition was coated onto 90 g/m² Kraft medical grade paper using a 0.5 mil (1.3 mm) knife. The final dried laydown was 0.59 g/m² of Activator Ink Part B and 0.43 g/m² of Reactive Ink Part A.

The coated indicator compositions of Invention Examples 10 and 11, Comparative Examples 4 and 5 were cut as films and sealed with a polypropylene/polyester bilayer film, and were subjected to sterilization conditions and analyzed as described above in Print Sample Preparation.

Sterilization Results:

The data in the following TABLE III show that encapsulating the activator component (first reactant) within porous inorganic polymeric particles according to the present invention significantly slowed the chemical reaction with the second reactant (that causes the color change through the formation of the metal sulfide) by about a factor of 1.5-2 as measured by $\Delta L^*$ and $\Delta E$ compared to Comparative Examples 4 and 5.

TABLE III

| Parameter at 18 minutes at 135° C. in Sterilizer | $L^*$ $\Delta$ from Fresh | $\Delta E$ from Fresh |
|---|---|---|
| Comparative Example 4 (milled inks) | −43 | 46 |
| Comparative Example 5 (unmilled inks) | −43 | 47 |
| Invention Example 10 | −30 | 38 |
| Invention Example 11 | −18 | 29 |

The invention has been described in detail with particular reference to certain preferred embodiments thereof, but it will be understood that variations and modifications can be effected within the spirit and scope of the invention.

The invention claimed is:

1. A method for indicating an environmental condition stimulus, the method comprising:
    exposing an indicator composition to electromagnetic radiation, saturated steam, ethylene oxide, formaldehyde, dry heat greater than 100° C., or any combination of these environmental condition stimuli, sufficient to cause a detectable change in the indicator composition, the indicator composition comprising:
    a) a first polymeric particle comprising a solid continuous polymeric phase, multiple discrete compartments that are not interconnected and are dispersed within the solid continuous polymeric phase, and a first solid particle reactant within the volume of the multiple discrete compartments, the first polymeric particle having a mode particle size equal to or less than 50 mm; and
    b) a second solid particle reactant that is outside of the first polymeric particle, which second solid particle reactant is capable of reacting with the first solid particle reactant when exposed to the electromagnetic radiation, saturated steam, ethylene oxide, formaldehyde, dry heat greater than 100° C., or any combination of these environmental condition stimuli,
    wherein the indicator composition further comprises an organic polymeric matrix in which the first polymeric particle is dispersed, and the second solid particle reactant is predominantly within the organic polymeric matrix.

2. The method of claim 1, comprising exposing the indicator composition for more than 1 minute to saturated steam or dry heat above 100° C. as the environmental condition stimulus.

3. The method of claim 1, comprising exposing the indicator composition to the electromagnetic radiation, saturated steam, ethylene oxide, formaldehyde, dry heat greater than 100° C., or any combination of these environmental condition stimuli sufficient to cause a detectable color change in the indicator composition, which detectable color change is a change from a colorless state to a colored state, from a colored state to a colorless state, or from one color hue to another color hue.

4. The method of claim 1, comprising exposing the indicator composition to ethylene oxide as the environmental condition stimulus.

5. The method of claim 1, comprising exposing the indicator composition to the electromagnetic radiation, saturated steam, ethylene oxide, formaldehyde, dry heat greater than 100° C., or any combination of these environmental condition stimuli sufficient to provide the color change by the formation of insoluble metal sulfides.

6. The method of claim 1, wherein the first solid particle reactant is a source of a sulfide and the second solid particle reactant is reactive with the sulfide.

7. The method of claim 1, comprising exposing the indicator composition to the electromagnetic radiation, saturated steam, ethylene oxide, formaldehyde, dry heat greater than 100° C., or any combination of these environmental condition stimuli sufficient to cause a reaction of the second solid particle reactant with the first solid particle reactant to provide a color change outside the first polymeric particle.

8. The method of claim 1, comprising exposing the indicator composition to the electromagnetic radiation, saturated steam, ethylene oxide, formaldehyde, dry heat greater than 100° C., or any combination of these environmental condition stimuli to cause a reaction of the second solid particle reactant with the first solid particle reactant via an intermediate reaction product of either the first or second reactant.

9. The method of claim 1, comprising exposing the indicator composition to the electromagnetic radiation, saturated steam, ethylene oxide, formaldehyde, dry heat greater than 100° C., or any combination of these environmental condition stimuli to cause a change in color in the indicator composition, which change in color is accomplished by hiding the original color of the indicator composition.

10. The method of claim 1, wherein the second solid particle reactant is present within a second polymeric particle that comprises a solid continuous polymeric phase and one or more discrete compartments dispersed within the solid continuous polymeric phase, which second solid particle reactant is present predominantly within the volume of the one or more discrete compartments within the second polymeric particle.

11. The method of claim 1, wherein the first polymeric particle has a mode particle size of at least 1 μm and up to and including 20 μm.

12. The method of claim 1, wherein the first polymeric particle further comprises an inert colorant.

13. The method of claim 1, wherein the solid continuous polymeric phase of the first polymeric particle comprises one or more organic polymers.

14. The method of claim 1, for sterilizing surgical instruments or clothing, wherein the indicator composition is present in a pouch containing the surgical instruments or clothing, or the indicator composition is present as a label or free standing web in the pouch.

15. A method for indicating an environmental condition stimulus, the method comprising:
exposing an indicator composition to electromagnetic radiation, saturated steam, ethylene oxide, formaldehyde, dry heat greater than 100° C., or any combination of these environmental condition stimuli, sufficient to cause a detectable change in the indicator composition, the indicator composition comprising:
a) a first polymeric particle comprising a solid continuous polymeric phase, multiple discrete compartments that are not interconnected and are dispersed within the solid continuous polymeric phase, and a first reactant within the volume of the multiple discrete compartments, the first polymeric particle having a mode particle size equal to or less than 50 μm; and
b) a second reactant that is outside of the first polymeric particle, which second reactant is capable of reacting with the first reactant when exposed to the electromagnetic radiation, saturated steam, ethylene oxide, formaldehyde, dry heat greater than 100° C., or any combination of these environmental condition stimuli,
wherein the solid continuous polymeric phase of the first polymeric particle comprises one or more inorganic polymers.

16. The method of claim 15, wherein the indicator composition further comprises an organic polymeric matrix.

* * * * *